United States Patent
Henco et al.

(10) Patent No.: US 9,439,998 B2
(45) Date of Patent: Sep. 13, 2016

(54) COMPOSITIONS AND METHODS FOR DISINFECTING MATERIALS

(75) Inventors: Karsten Henco, Düsseldorf (DE); Thomas Freier, Mainz (DE); Rivelino Montenegro, Mainz (DE)

(73) Assignee: Medoderm GmbH, Mainz (DE)

(*) Notice: Subject to any disclaimer, the term of this patent is extended or adjusted under 35 U.S.C. 154(b) by 0 days.

(21) Appl. No.: 13/393,520

(22) PCT Filed: Sep. 1, 2010

(86) PCT No.: PCT/EP2010/005369
§ 371 (c)(1),
(2), (4) Date: May 14, 2012

(87) PCT Pub. No.: WO2011/026614
PCT Pub. Date: Mar. 10, 2011

(65) Prior Publication Data
US 2012/0252755 A1    Oct. 4, 2012

(30) Foreign Application Priority Data
Sep. 4, 2009   (WO) ................. PCT/EP2009/006323

(51) Int. Cl.
*A01N 43/16* (2006.01)
*C08B 37/08* (2006.01)
*A61P 17/02* (2006.01)
*A61K 31/722* (2006.01)
*A61L 15/28* (2006.01)
*A61L 26/00* (2006.01)

(52) U.S. Cl.
CPC ............ *A61L 15/28* (2013.01); *A61L 26/0023* (2013.01)

(58) Field of Classification Search
USPC .............................................. 514/55; 536/20
See application file for complete search history.

(56) References Cited

U.S. PATENT DOCUMENTS

| | | |
|---|---|---|
| 2002/0018732 A1* | 2/2002 | Hung et al. ................ 422/28 |
| 2003/0022573 A1 | 1/2003 | Cintio et al. |
| 2005/0042265 A1* | 2/2005 | Guillot et al. ............ 424/445 |
| 2009/0117213 A1 | 5/2009 | Beaulieu et al. |

FOREIGN PATENT DOCUMENTS

| | | | | |
|---|---|---|---|---|
| JP | 61-268626 | * | 11/1986 | ........... A61K 31/715 |
| WO | 2008/072230 A1 | | 6/2008 | |
| WO | 2008072230 A1 | | 6/2008 | |
| WO | WO 2008/072230 A1 | * | 6/2008 | ............ A61K 47/36 |
| WO | 2009/028965 A1 | | 3/2009 | |
| WO | 2010021930 A1 | | 2/2010 | |

OTHER PUBLICATIONS

The Merck Manual, 1992, pp. 183-189.*
Minagawa et al, Carbohydrate Polymers, 2007, 67, 640-644.*
International Search Report and Written Opinion issued in PCT/EP2010/005369 on Mar. 3, 2011.
Minagawa et al., "Effects of molecular weight and deacetylation degree of chitin/chitosan on wound healing", Carbohydragte Polymers, 2007, 67(4):640-644.
Aranaz et al., Functional Characterization of Chitin and Chitosan. Curr Chem Biol. 2009;3:203-230.
Cooper, The Plaque Assay of Animal Viruses. Adv Virus Res. 1961;8: 319-78.
Kumar, A review of chitin and chitosan applications. React Funct Polym. Nov. 2000;46(1):1-27.
Lavertu et al., A validated 1H NMR method for the determination of the degree of deacetylation of chitosan. J Pharm Biomed Anal. Aug. 21, 2003;32(6):1149-1158.
Shigemasa and Minami, Applications of Chitin and Chitosan for Biomaterials. Biotech Genetic Eng Rev. 1996;13:383-420.
Singh and Ray, Biomedical Applications of Chitin, Chitosan and Their Derivatives. J Macromol Sci. 2000;C40(1):69-83.
Park et al., *Journal of Microbiology and Biotechnology*, 14(2): 317-323 (2004).

* cited by examiner

*Primary Examiner* — Ganapathy Krishnan
(74) *Attorney, Agent, or Firm* — Leydig, Voit & Mayer, Ltd.

(57) ABSTRACT

The present invention relates to methods for disinfecting or decontaminating a material or for preventing an infection or contamination of a material. The invention further relates to compositions which are suitable for disinfecting a material or for preventing an infection or contamination of a material and to uses of such compositions. The invention further relates to a medical use of chitosan and to a pharmaceutical composition comprising the chitosan. The invention further relates to a method of treating a microbial infection and to an aqueous solution comprising chitosan. The invention moreover relates to a chitosan or a pharmaceutical composition comprising a chitosan for an epithelial cell growth stimulating treatment of a patient's tissue and to a method of stimulating the growth of epithelial cells. The invention also relates to a tissue dressing material.

44 Claims, 12 Drawing Sheets

COMPOSITIONS AND METHODS FOR DISINFECTING MATERIALS

RELATED APPLICATIONS

This application is filed under 35 U.S.C. §371 as the U.S. national phase of International Application PCT/EP2010/005369, filed Sep. 1, 2010, which designated the U.S. and claims priority to the International Application PCT/EP2009/006323, filed Sep. 1, 2009. The entire disclosure of both applications, including the drawings, is hereby incorporated herein by reference.

SUBJECT OF THE INVENTION

The present invention relates to methods for disinfecting or decontaminating a material or for preventing an infection or contamination of a material. The invention further relates to compositions which are suitable for disinfecting a material or for preventing an infection or contamination of a material and to uses of such compositions.

The invention further relates to a medical use of chitosan and to a pharmaceutical composition comprising the chitosan. The invention also relates to a method of treating a microbial infection and to an aqueous solution comprising chitosan. The invention moreover relates to a chitosan or a pharmaceutical composition comprising a chitosan for an epithelial cell growth stimulating treatment of a patient's tissue and to a method of stimulating the growth of epithelial cells. The invention also relates to a tissue dressing material.

BACKGROUND OF THE INVENTION

The polysaccharide chitosan is the at least partially N-deacetylated derivative of chitin. Chitin can be found widely in the exoskeletons of arthropods, crustaceans and the cuticles of insects. It is usually derived from such natural sources. Chitosan in general is synthetically prepared by hydrolysis of chitin, although it can also be naturally derived directly, e.g. from certain fungi in which it occurs. The different solubilities of chitin and chitosan in dilute acids are commonly used to distinguish between the two polysaccharides. Chitosan, the soluble form, can have a degree of acetylation (DA) between 0% and about 60%, the upper limit depending on parameters such as processing conditions, molecular weight, and solvent characteristics. While soluble in acidic aqueous media, chitosan precipitates at a pH of above 6.3.

Both chitin and chitosan are promising polymers for biomedical applications because of their biocompatibility, biodegradability and structural similarity to the glycosaminoglycans. For comprehensive reviews of potential applications of chitin and chitosan see, e.g., Shigemasa and Minami, "Applications of chitin and chitosan for biomaterials", Biotech. Genetic. Eng. Rev. 1996, 13, 383; Kumar, "A review of chitin and chitosan applications", React. Funct. Polym. 2000, 46(1), 1; and Singh and Ray, "Biomedical applications of chitin, chitosan and their derivatives", J. Macromol. Sci. 2000, C40(1), 69.

Aranaz et al. in "Functional characterization of chitin and chitosan", Curr. Chem. Biol. 2009, 3, 203, discuss the antimicrobial activity of chitosan, including activity against bacteria, yeast, and fungi. A first mechanism discussed involves an interaction with the cell surface of gram-negative bacteria, which interaction is believed to prevent the transport of essential solutes. Another mechanism involves an inhibition of RNA and protein synthesis in the cell nucleus. This theory appears to predict that a relatively low molecular weight and a relatively low degree of acetylation should increase the chitosan's activity. It is, however, also pointed out that some authors have not found a clear relationship between the degree of acetylation and the antimicrobial activity of chitosan. E.g., in a study by Parker et al. 25% acetylated chitosan showed more effective antimicrobial activity compared with that of 10% and 50% acetylated chitosan. Other suggested mechanisms involve the activity of chitosan as a chelating agent, chitosan's activity to interact with flocculate proteins, and a direct disturbance of membrane function in fungi.

The patent application WO 2010/021930 A1 discloses activity of several chitosan derivatives against bacteria including methicillin-resistant *Staphylococcus aureus*.

The patent application US 2009/0117213 A1 discloses a chitosan/alcohol solution that has antiviral, antibacterial and hemostatic effects. In particular, a solution comprising 1.5% chitosan with a molecular weight between 150 and 300 kD (kilodalton) and a degree of acetylation of 5%, the solution further comprising 25% v/v ethyl alcohol showed antibiotic activity in vitro against several strains of bacteria, including moderate activity against methicillin-resistant *Staphylococcus aureus*.

Formulations of pharmaceutically or biologically active compounds are typically applied in a concentration which is higher than the concentration to be realized at the site of action, i.e. the effective or pharmaceutical concentration. This is due to the fact that once administered to an organism or any other site of application, e.g. an inanimate material, such formulations are typically subject of dilution before reaching the site of action.

Typical concentrations of pharmaceuticals at the biological site of action are considered less than $\mu M$ concentrations. A 1 $\mu M$ concentration of a molecule having a molecular weight of 100 D corresponds to a concentration of 0.0001 g/l or 0.000010% w/v (weight per volume). As a consequence, pharmaceutical compounds acting systemically and being associated with high bioavailability upon administration can be given as tablets of mg weights, such as corticosteroids. Such pharmaceutically or biologically active compounds are often and typically associated with adverse effects at higher concentrations. The window of therapeutically acceptable concentrations at the site of action is called therapeutic index. A number of compounds provide such a small therapeutic index that they need to be administered at almost pharmaceutical concentrations as infusion over time with immediate dilution upon infusion.

Some biologically active compounds are only active at concentrations which may not be practicable for a systemic application. An upper limit of practicability is given by compounds such as vitamin C or omega-3-unsaturated fatty acid which can be administered orally in gram amounts per individual. Saccharose with its potential to effectively block fungal or bacterial growth at concentrations of higher than about 30% can be used as a preservative in neutraceuticals or for stabilization of sensitive proteins, but is not suitable for the treatment of living material or organisms.

Chitosan requires a relatively high concentration at the site of action in order to exert a microbial effect but still provides a large therapeutic index. However, on the one hand, there is a common understanding in the prior art that the concentration of active ingredients in the composition to be applied non-systemically must be higher than required at the site of action due to dilution effects. Further, in view of that there are concerns that a poor solubility of chitosan in a pharmaceutically or biologically acceptable solvent may become a limiting factor for achieving a satisfactory microbial effect on or in the material to be treated. On the other hand, for therapeutic or prophylactic applications in humans the need for relatively high concentrations of chitosan at the site of action implies that introducing chitosan in the systemic circulation should be avoided.

Accordingly, there is a need for alternative compositions and methods for disinfecting or decontaminating materials harboring pathogenic microorganisms such as bacteria, fungi or viruses.

OBJECT AND SUMMARY OF THE INVENTION

It is an object of the present invention to provide an easy-to-accomplish, inexpensive and sustainable method for disinfecting or decontaminating materials harboring pathogenic microorganisms or preventing an infection or contamination of materials with pathogenic microorganisms. Furthermore, it is an object of the present invention to provide compositions which are suitable to be used in such methods.

It is a further object of the invention to provide a new medical use of a chitosan. The invention further aims at providing an improved pharmaceutical composition comprising chitosan for a medical use. Moreover, the invention seeks to provide a new method of treating a microbial infection and an improved pharmaceutical form of chitosan. It is a further object of the invention to provide a new method of stimulating the growth of epithelial cells. It is another object of the invention to provide an improved tissue dressing material and an improved tissue dressing material.

These objectives as well as others which will become apparent from the ensuing description are attained by the subject matter of the independent claims. Some of the embodiments of the present invention are defined by the subject matter of the dependent claims.

In particular, compositions having low concentrations of chitosan and methods involving the use of such composition are provided which are efficient in disinfecting or decontaminating a material or preventing an infection or contamination of a material. Such an infection or contamination may be a microbial infection or contamination, e.g. a bacterial, fungal or viral infection or contamination.

In particular, it has been surprisingly found that contacting low concentrated chitosan compositions with a material to be disinfected or decontaminated leads to an efficient concentration of an antimicrobially active chitosan at a surface or interface of the material. The chitosan content of the composition which may optionally be applied as an aqueous solution free of alcohol or organic solubilizer can be enriched by forming a deposit, e.g. a solid or gel-like amorphous structure, of a first fraction of the chitosan on or in the material to be treated before the composition is brought in contact with the material or by in situ formation of the deposit on the surface or interface of the material to be treated. The deposit may be formed by shifting the pH of the composition towards a neutral or basic pH. The pH shift may be caused by contacting the composition with the surface or interface of the material to be treated which may have a pH in the physiological range, e.g. from about 6.0 to about 8.0. Further, the formation of a deposit of a first fraction of chitosan may be accompanied and/or followed and/or induced by evaporation of a solvent contained in the chitosan composition.

For example, a less than 3% aqueous solution may instantly form a gel type deposit on or in a material having a pH in the range of from 6.5 to 8 or higher due to the insolubility of a first fraction of chitosan at a pH in that range. This process of forming a deposit may involve the inclusion of a water soluble second chitosan fraction in the deposit. Due to solvent evaporation chitosan contained in the composition may be concentrated or enriched from less than 3% to a final concentration in the deposit of up to 100% chitosan. The deposit may contain molecularly hydrated chitosan. This deposit or gel usually remains dry due to the lack of hygroscopic properties of chitosan.

The compounds and methods of the present invention are suitable to expose microbial entities such as bacteria, viruses or fungi to high concentrations of chitosan at surfaces or interfaces of μm dimensions. In particular, a second fraction of soluble chitosan may be slowly released from its deposit- or gel-trapped highly concentrated form of a first fraction and penetrate into the material to be treated. In view of its molecular weight and hydrodynamic radius penetration such as diffusion may only occur in distances in the μM range. As a result those microorganisms will be effectively treated which are present directly at the insoluble chitosan surface or in the interface of the material having a high concentration of the second fraction of chitosan released from the deposit of the first fraction.

Infections or contaminations of surfaces or interface regions of a material may play an important economic and/or medicinal role. In particular, a number of infections such as multi resistent *Staphylococcus aureus* (MRSA) related infections mainly affect the outer surface of wounds, cuts or stitched wounds after surgical closure, technical surfaces, fibers, tissues or walls.

In one aspect, the present invention relates to a composition for treating a material, wherein the composition comprises a chitosan, and a first fraction of the chitosan is configured to form a deposit on a surface of the material and/or is insoluble in the material and a second fraction of the chitosan is configured to penetrate into and/or is soluble in the material.

A treatment within the meaning of the present invention includes disinfecting or decontaminating or sterilizing a material harboring pathogenic microorganisms and/or preventing infections or contaminations with pathogenic microorganisms. In particular, the terms "disinfecting" or "decontaminating" or "sterilizing" can be used as synonyms within the meaning of the present invention. The terms "infection" or "disinfecting" may also be used in connection with the treatment of living material such as human tissue. The terms "contamination" and "decontaminating" may also be used in connection with the treatment of non-living or inanimate material such as medical equipment or drinking water.

A material may be considered to be disinfected or decontaminated within the meaning of the present invention if the number of viable microorganisms is less than 30 CFU or PFU per ml or g of the material, e.g. less than 20 CFU or PFU per ml or g of the material or less than 10 CFU or PFU per ml or g of the material or less than 5 CFU or PFU per ml or g of the material.

Colony-forming unit (CFU or cfu) is a measure of viable bacterial or fungal numbers. Unlike direct microscopic counts where all cells, dead and living, are counted, CFU measures viable cells. For convenience the results are given as CFU/mL (colony-forming units per milliliter) for liquids, and CFU/g (colony-forming units per gram) for solids. Methods for determining colony-forming units are well known to the person skilled in the art. Microorganisms may be quantitated by cultivating methods. E.g., a dilution made with bacteria and peptoned water is placed in an Agar plate (Agar plate count for food samples or Trypticase soy agar for clinic samples) and spread uniformly over the plate so that individuals of the microorganisms may form a colony by growth and propagation under suitable culture conditions. Under ideal conditions the number of colonies corresponds to the number of individuals of the microorganisms in the sample.

Plaque forming unit (PFU or pfu) is a measure of infectious viruses (infectious units) in a sample. Plaque assays for determining plaque-forming units are well known to the person skilled in the art (see e.g. P. D. Cooper: The plaque assay of animal viruses. Adv Virus Res 8: S. 319-78).

The composition according to the present invention may be a pharmaceutical composition.

Pathogenic microorganisms within the meaning of the present invention include bacteria, fungi or viruses such as multi resistant *S. aureus* (MRSA), *E. coli, P. aeruginosa* and/or *B. tuberculosis*.

Materials to be treated include solid or fluid materials. Solid materials include surfaces or interface regions of living or non-living materials. In particular, the solid material is a hydrophilic material and/or has a hydrophilic surface or interface region. Exemplary hydrophilic materials include but are not limited to a healthy skin, a microbially infected skin, a wound, cavities of the human body which are externally accessible without surgical steps, but e.g. via inhalation, such as cavities belonging to the nose, ear, throat and respiratory system including the lung, surfaces or interfaces of inanimated material such as but not limited to walls, plastic or metal surfaces, and tissues. Fluid materials include aqueous solutions or suspensions such as drinking water. In case an aqueous solution or aqueous suspensions is to be treated the surface or interface of the material shall mean the interface of such deposits of the first fraction of the chitosan formed as e.g. gel-type droplets surrounded by the interface of the solvent of such a solution or suspension.

E.g., the material to be treated may be a hydrophilic material or an aqueous solution or suspension.

In some embodiments, the composition may be applied to the material in liquid form, e.g. as an aqueous solution. In particular, the composition may be an aqueous solution which does not contain an alcohol. In addition or alternatively, this aqueous solution comprising the chitosan may have a pH of 5 to 6, optionally of about 5.5.

The first fraction of chitosan of the composition according to the present invention may be in a form that is insoluble at a pH of 6.5 or higher.

Further, the second fraction of chitosan of the composition according to the present invention may be in a form that is soluble at a pH of 6.5 to 8.

In another embodiment. the composition is a liquid having a low concentration of the chitosan, e.g. a concentration of the chitosan from about 0.05% w/v to about 5.0% w/v, e.g. from about 0.5% w/v to about 3.0% w/v or from about 0.75% w/v to about 1.0% w/v.

In some embodiments, the deposit or gel type repository structure of the first fraction of chitosan may also facilitate redissolution of the second soluble fraction of chitosan by trapping the soluble molecule in the deposit or gel type, e.g. amorphous structure and then releasing it into the material over time.

In still another embodiment the composition according to the present invention is aerolisable, suspensable, sprayable and/or inhalable.

Another aspect of the present invention relates to a method of disinfecting or decontaminating a material or preventing an infection or contamination of a material comprising the following steps:

a) providing a composition having a concentration of a chitosan which is equal to or lower than an effective concentration of the chitosan for disinfecting or decontaminating the material or preventing an infection or contamination of the material;
b) contacting the composition with the material.

Within the context of the present invention an effective concentration of the chitosan refers to the concentration of active chitosan at a site of action, e.g. on a surface or in an interface region of the material to be treated.

Within the context of the present invention an active or biologically active chitosan includes a chitosan which is soluble in the material or in interface region of the material.

The material to be treated may have a pH which is different from that of the chitosan composition. In particular, the material may have a pH in the physiological range, e.g. from about 6.0 to about 8.0. Further, the chitosan composition may have a pH in the range of about 4.5 to about 5.9.

The method of the present invention may further comprise a step c) of forming a deposit of a first fraction of the chitosan on a surface of the material or forming a deposit of a first fraction of the chitosan in the material. In particular, the deposit may be a solid or gel-like precipitate on a surface of the material (if the material is a solid) or in the material (if the material is a fluid). The deposit may be formed by shifting the pH of the composition towards a neutral or basic pH. The pH shift may be caused by contacting the composition with the surface or interface of the material to be treated which may have a pH in the physiological range.

Step c) of the method of the present invention may further comprise evaporating a solvent contained in the deposit. In particular, the solvent may be essentially completely evaporated.

The method may further comprise transporting a second fraction of the chitosan into the material. Transporting may occur via penetration, diffusion, convection and/or other transport mechanisms.

Alternatively, the method may further comprise dissolving a second fraction of the chitosan in the material.

Further, the composition may be administered topically or may be applied drop-wise or by aerolizing, suspending or spraying. Topical administration includes the use of patches, e.g. medical patches or other wound dressings comprising the above chitosan composition of the present invention.

In some embodiments of the invention, the chitosan or chitosan containing composition may be applied to the patient in vivo. Alternatively, it may be applied ex vivo to an epithelial cell containing cell culture.

In another embodiment. the composition is a liquid having a low concentration of the chitosan, e.g. a concentration of the chitosan from about 0.05% w/v to about 5.0% w/v, e.g. from about 0.5% w/v to about 3.0% w/v or from about 0.75% w/v to about 1.0% w/v.

In another embodiment, the material may be an aqueous solution or suspension.

In still another embodiment, the material may be an inanimate material, e.g. selected from the group consisting of a door handle, a clothing, a wallpaper, a medical gown, a medical facecover, a hydrophilic surface in a hospital room, medical equipment such a medical instrument, a stent, an implant, a container such as a bottle or a tube comprising infusion solutions or an incubator, and materials found or used in animal breeding facilities.

In further aspects, the composition according to the present invention are provided for use as a medicament. Specific medical uses include but are not limited to the use in the treatment of wounds, the use in tissue repair or tissue remodeling of wounds, the use in disinfecting wounds, the use in promoting hemostasis, the simultaneous use in promoting hemostasis, disinfecting wounds and repairing the tissue of wounds, and/or the use in the prevention or treatment of microbial infections.

Further uses of the composition according to the present invention include but are not limited to disinfecting of solutions selected from the group consisting of an infusion, a nutrition solution and a neutraceutical solution, and disinfecting or preventing a microbial infection of drinking water for human or animal use.

In another aspect, the present invention relates to a chitosan for use in an antimicrobial treatment of a patient's tissue. Further, the present invention relates to a pharmaceutical composition comprising a chitosan for use in an antimicrobial treatment of a patient's tissue.

The invention further provides a method of treating a microbial infection, the method comprising the step of administering to a patient an effective amount of a chitosan. The problem is moreover solved by providing an aqueous solution comprising chitosan.

Thereby, the antimicrobial properties of the chitosan are exploited.

The invention further provides a chitosan or a pharmaceutical composition comprising a chitosan for use in an epithelial cell growth stimulating treatment of a patient's tissue. The invention further provides a method of stimulating the growth of epithelial cells, the method comprising the step of administering to a patient an effective amount of a chitosan or a pharmaceutical composition comprising chitosan. Thereby, the epithelial cell growth stimulation properties of chitosan are exploited. The epithelial cells may be human epithelial cells. The epithelial cells may be keratinocytes.

In one embodiment, the chitosan and the pharmaceutical composition according to the invention can simultaneously provide for an antimicrobial treatment and an epithelial cell growth stimulating treatment. This may be useful in the treatment of wounds of various types. Some suitable types of wounds are listed further below in the discussion of preferred embodiments of the invention.

The invention further provides a tissue dressing material that consists of chitosan and a tissue dressing material that is a composition comprising chitosan. Due to the antimicrobial properties of the chitosan the tissue dressing material according to the invention can be kept essentially free of a broad range of microbes without the addition of further antimicrobial or antibiotic substances to the tissue dressing material. In particular, the tissue dressing material according to the invention can be kept sterile according to the pertinent hygienic requirements without the addition of further antimicrobial or antibiotic substances to the tissue dressing material.

The tissue dressing material may be used for dressing wounds. In particular, the tissue dressing material can be used for an antimicrobial and/or an epithelial cell stimulating treatment according to the invention.

A patient in the context of the present invention can be a human or an animal.

FIGURE LEGENDS

The invention is illustrated in greater detail with the aid of the following figures.

Figure 10:
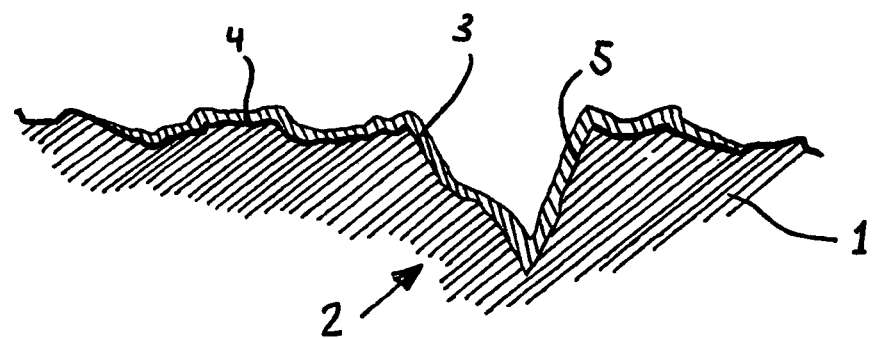
Figure 11:
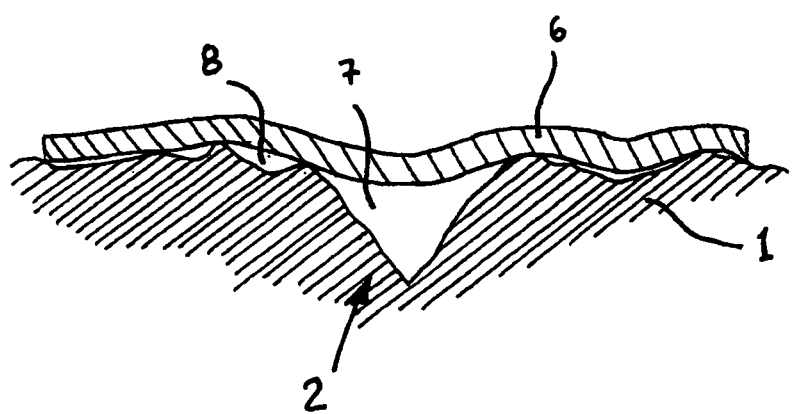
Figure 12:
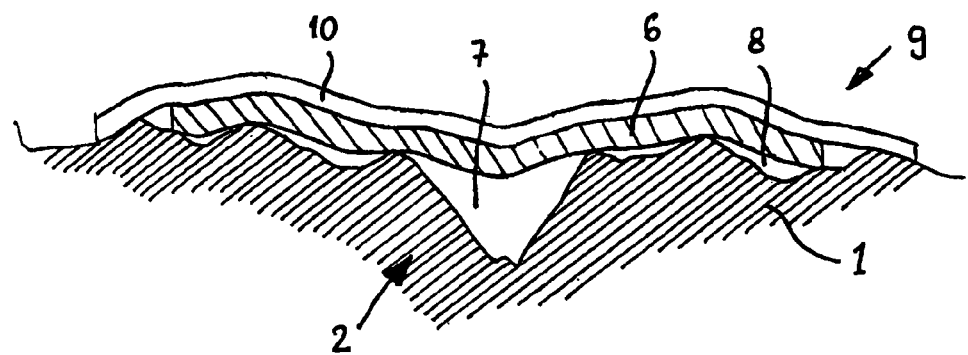
Figure 13:
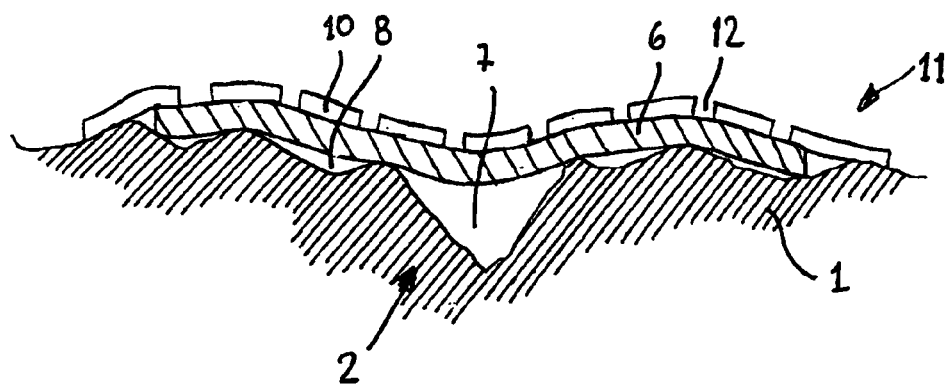
Figure 14:
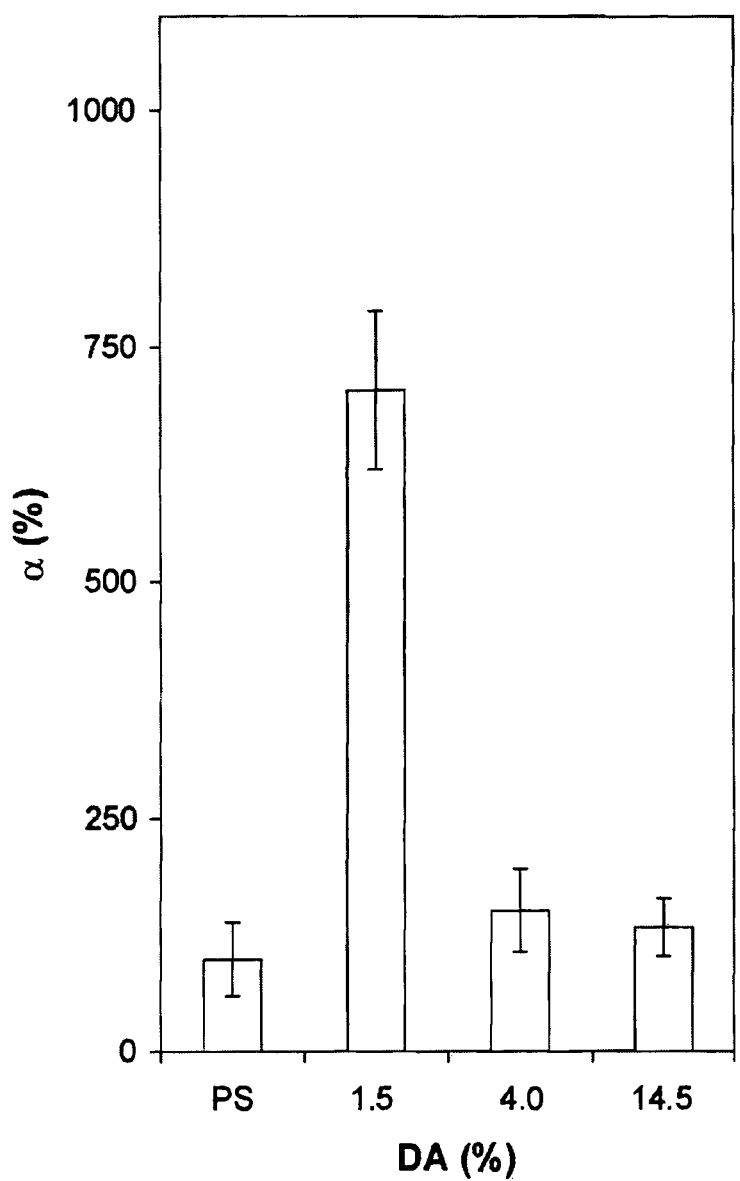
Figure 15:
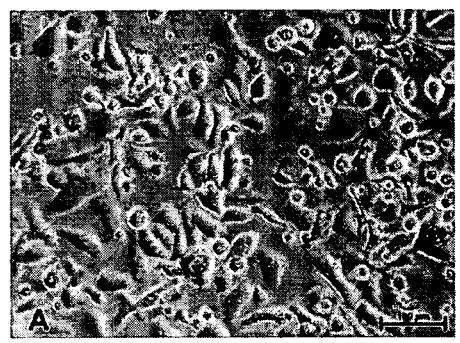
Figure 15:
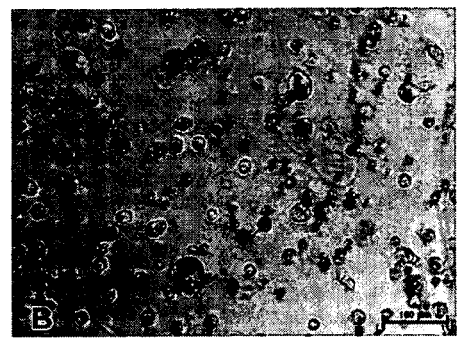

FIG. 10 schematically illustrates a wound to which a liquid chitosan containing composition according to the inventions has been applied;

FIG. 11 schematically illustrates a wound to which a solid chitosan material according to the inventions has been applied;

FIG. 12 schematically illustrates a wound to which a non-perforated wound dressing according to the invention has been applied;

FIG. 13 schematically illustrates a wound to which a perforated wound dressing according to the invention has been applied;

FIG. 14 illustrates the cell viability of keratinocytes on chitosan materials of various degrees of acetylation, relative to tissue culture polystyrene controls (PS=100%);

FIG. 15 shows microscopic images of human keratinocytes grown on chitosan materials of various degrees of acetylation (A: 1.5%; B: 14.5%).

Figure 16:
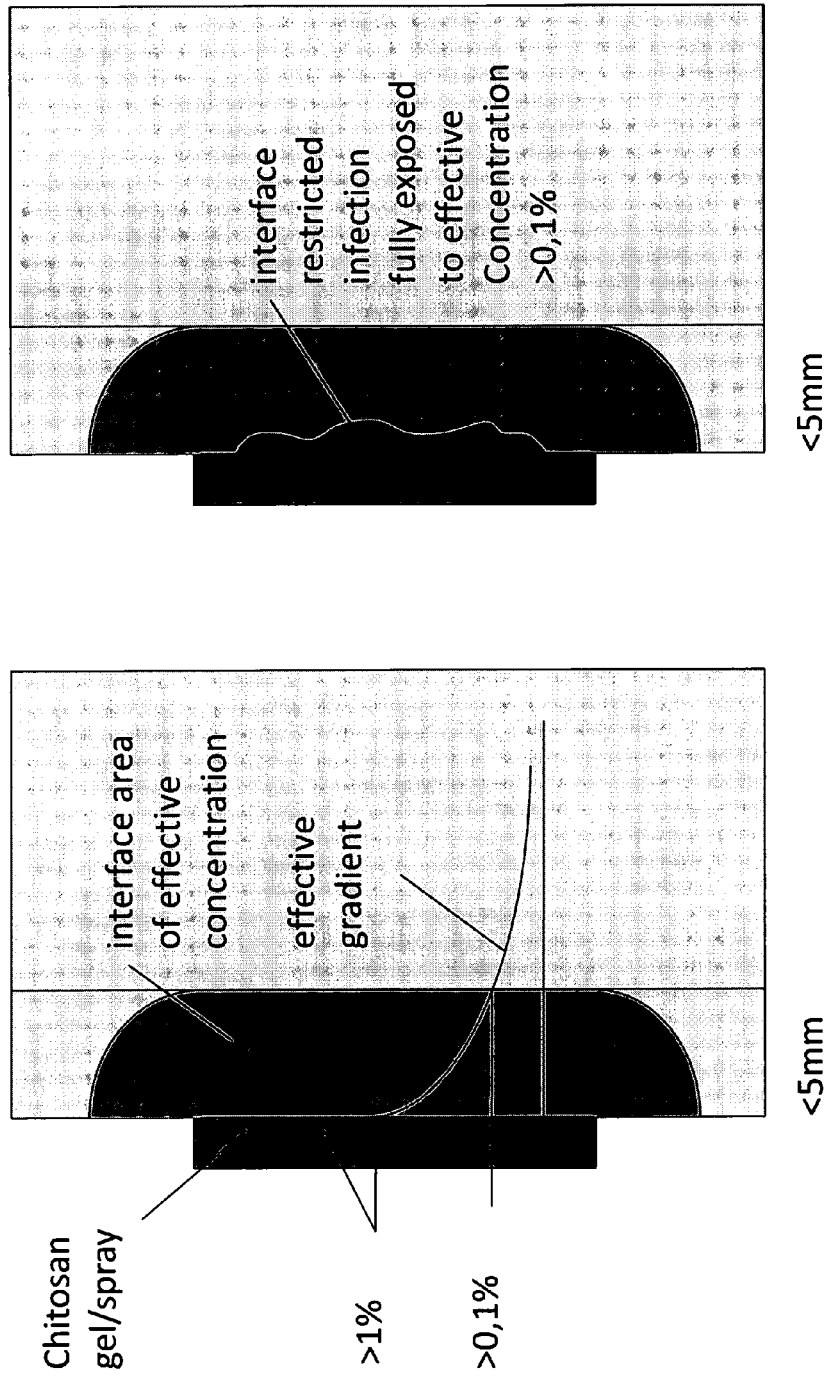

FIG. 16 schematically visualizes the topical effect of chitosan gel as an in situ formed gel or a preformed chitosan gel-layer associated with tissue surface (left). The dark area symbolized the stabile gradient of slowly diffusing soluble chitosan molecules setting up an effective antibiotic-type concentration of active chitosan restricted to an environment of <5 mm. Such environment is effective to treat a topical infection focused or restricted to just this environment of effective concentration (right).

DETAILED DESCRIPTION OF THE INVENTION

The present invention is partly based on the finding that, on the one hand, biologically active chitosan fractions only efficiently and irreversibly inhibit the proliferation of microbials at rather high concentrations of at least 0.1% w/v at the site of action. Such high concentrations are orders of magnitudes away from typical pharmaceutical compounds with effective concentrations less than 1 µM for systemic treatments. On the other hand, chitosan fractions and derivatives also being found in nature share the property of being safe and not associated with adverse side effects even at extremely high concentrations which means a large therapeutic index or large biological index.

In one embodiment, the invention provides a chitosan containing composition comprising an insoluble chitosan, which is also referred to as a first fraction of chitosan, which may release a second fraction of soluble components of slowly diffusing oligomers or low molecular weight polymers of the same basic type of chitosan polymer into the surrounding μm-dimensioned interface adjacent to an environment, e.g. a biological environment such as a solution, tissue, growing cell layers or blood. The release of the second fraction may be constant over time.

In particular, the compounds and methods according to the present invention may establish a high concentration of active chitosan in an interface compartment being formed in an interface of the material to be treated, such as a biological tissue or an aqueous solution, and limited on one side (usually the externally accessible side) by the deposit of insoluble chitosan as the source for such active chitosan.

Within the meaning of the present invention an interface region of the material includes a fiber shaped or layer shaped or droplet shaped volume with one dimension (usually the depth of the material to be treated) being optionally 2000 μm or less, e.g. 1000 μm or less. The depth of the material to be treated depends on the molecular weight of the biologically active component which, in turn, has an influence on the retention time within the interface region sufficient to exercise its biological activity before being diluted by diffusion, convection or other transport mechanisms. This retention time increases with an increasing molecular weight of the chitosan.

The compounds and methods of the present invention make use of the properties of chitosan as being topically applicable without any limit in concentration, being available for decontamination purposes at any quantity needed, lacking any substantial antigenic or allergenic potential and its ability to exert biological function as a stand-alone bioactive chemical. Thus, the compounds and methods of the present invention can be applied for topical medical treatment or prevention of microbial infections, but is not restricted to medical uses. E.g., the method can also be applied to suspensions containing living biological systems and to surfaces or thin layers belonging to living or non living material. The lack of creating resistency in nature also makes this method suitable for technical decontaminations on a large scale such as decontamination and/or prevention of decontamination of buildings or drinking water.

The compositions and methods of the present invention may also have a number of advantages from an ecological point of view. When used as an agent for decontamination on a large scale or as a preservative for drinking water, advantages include low cost and large volume availability of chitin or chitosan. The composition of the present invention may further be free of organic solubilizers or alcohol additives or any other reactive chemical such as peroxide, aldehyde, or chlorine and also usually do not have an extreme pH. Further, the composition of the present invention is typically free of any disturbing odor when used for large area decontaminations. It is also not etching, explosive or toxic in any way. Handling is safe even in inexperienced hands as there is no toxicity known in even the most concentrated form.

The method of the present invention also allows the application of diluted solutions forming active concentrations just on site of application. There is essentially no danger to generate allergies as humans and animals all seem to be immunologically insensitive or tolerant to chitosan. As it is non reactive in a chemical sense it can even be applied as decontaminant in cases where any DNA within the interface facing the decontaminating composition should remain in its integrated form for later identification purposes. A further important aspect in large scale application is the lack of inducing resistance in pathogens.

In one aspect, the present invention relates to a composition for treating a material, wherein the composition comprises a chitosan. A first fraction of the chitosan is configured to form a deposit on a surface of the material and/or is insoluble in the material and a second fraction of the chitosan is configured to penetrate into and/or is soluble in the material.

Another aspect relates to a method of disinfecting a material or preventing an infection or contamination of a material comprising the following the steps:

a) providing a composition having a concentration of a chitosan which is equal to or lower than an effective concentration for disinfecting the material or preventing an infection or contamination of the material;

b) contacting the composition with the material.

The compositions and methods of the present invention will now be described with respect to particular embodiments and with reference to certain drawings but the invention is not limited thereto.

Where the term "comprising" is used in the present description and claims, it does not exclude other elements or steps. For the purposes of the present invention, the term "consisting of" is considered to be an optional embodiment of the term "comprising of". If hereinafter a group is defined to comprise at least a certain number of embodiments, this is also to be understood to disclose a group which optionally consists only of these embodiments.

Where an indefinite or definite article is used when referring to a singular noun e.g. "a" or "an", "the", this includes a plural of that noun unless specifically stated.

The term "about" in the context of the present invention denotes an interval of accuracy that the person skilled in the art will understand to still ensure the technical effect of the feature in question. The term typically indicates deviation from the indicated numerical value of ±10%, and in some embodiments ±5%.

Furthermore, the terms first, second, third or a), b), c) and d) and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

Within the context of the present invention a biological index shall mean the difference between the effective concentration for irreversibly reducing microbials in a material such as surfaces or aqueous solutions and the concentration of any adverse effect not being tolerable for the respective application.

Within the context of the present invention such tube or fiber or layer type volume establishing an environment of a high concentration of bioactive compound in direct contact to an insoluble polymer surface or deposit providing a reservoir for such released bioactive compound is denoted as an interface. Further, within the context of the present invention, a surface includes the surface of the material treated or to be treated with the composition of the present invention by contacting the surface with the composition. The surface may also include an interface region below the surface having a depth of e.g. 0 to 2,000 μm. This interface region may be penetrated by soluble chitosan of the second fraction released from the insoluble first fraction of chitosan.

Further definitions of term will be given in the following in the context of which the terms are used.

In some embodiments of the invention, the chitosan or chitosan containing composition may be applied to a patient in vivo. Alternatively, it may be applied ex vivo to an epithelial cell containing cell culture.

An exemplary treatment is for at least one of the following or a combination thereof: preventing the risk of a microbial infection, reducing the microbial load of an existing microbial infection, preventing or reducing the spread of a microbial infection. The chitosan or the pharmaceutical composition according to the invention may act as a barrier to protect of a microbial infection from inside and outside the tissue treated.

The infection or contamination may be a bacterial, fungal or viral infection or contamination. In particular, the infection or contamination may be caused by multi resistant *S. aureus* (MRSA), *E. coli*, *P. aeruginosa* and/or *B. tuberculosis*.

The antimicrobial treatment may be an antibacterial treatment, exploiting the antibiotic property of the chitosan. Exemplary indications include nosocomial infections or infections with multidrug resistant bacterial strains. The infection may be at least one of the following or a combination thereof: methicillin-resistant or multi-resistant *Staphylococcus aureus* (MRSA) infection, oxacillin-resistant *Staphylococcus aureus* (ORSA) infection, multidrug-resistant *Clostridium difficile* infection, penicillin-resistant *Streptococcus pneumonia* infection, multidrug-resistant *Pseudomonas aeruginosa* infection, multidrug-resistant *Acinetobacter baumannii* infection, vancomycin-resistant *Enterococcus* infection. Suitable bacteria include gram-positive bacteria, gram-negative bacteria and spore forming bacteria. Suitable bacteria include, for example, *Staphylococcus aureus*, *Streptococci* (group A), *Streptococcus pyogenes*, *Borellia burgdorferi*, *Bacillus anthracis*, *Erysopelothrix rhusiopathiae*, *Bartonella henselae*, *Bartonella quintana*, *Corynebacterium minutissimum*, *Staphylococcus epidermides*, Enterobacteriaceae (*E. coli*, *Klebsiella*), *Haemophilus influenzae*, *Pasteurella multocida*, *Franciscella tularensis*, *Pseudomonas aeruginosa*. The terms Methicillin-resistant *Staphylococcus aureus* and multi-resistant *Staphylococcus aureus* can be used synonymously.

However, the anti-microbial treatment may also be an antifungal treatment, e.g. against fungi involved in the athlete's foot disease such as dermatophytes or a treatment against. Suitable fungi and yeast include, for example, *Aspergillus niger*, *Mucor* (*Mucor pusillus*, *Mucor plumbeus*, *Mucor racemosus*, *Mucor hiemalis*), *Sporothrix*, *Histoplasma*, *Coccidioides*, *Trichophyton*, *Microsporum*, *Epidermophyton*, *Keratomyces*, *Cryptococcus*, *Candida albicans*, *Candida dubliensis*, *Malassezia furfur*.

The antimicrobial treatment may also be an antiviral treatment, exploiting the antiviral property of the chitosan. The infection may be at least one of the following or a combination thereof: HIV, herpes viruses, hepatitis B or C viruses, and influenza A or B viruses.

Similarly, the tissue dressing material according to the invention due to the presence of chitosan can be kept essentially free of the above cited microbes without the addition of other antimicrobial or antibiotic substances to the tissue dressing material.

The treatment may be a locally confined treatment. "Local confined" in the context of the present invention means that the activity of the chitosan or the chitosan containing composition is essentially limited to this tissue to which it is applied and tissue adjacent to the tissue to which it is applied. E.g., the adjacent tissue, where the chitosan or the chitosan containing composition is also active extends not more than 10 mm (millimeters), or not more than 5 mm away from the tissue to which the chitosan or the chitosan containing composition is applied. Such activity in adjacent tissue can for example be the result of transport (e.g. by diffusion, capillary forces, osmotic transport, cavitation) of active constituents of the chitosan or the chitosan containing composition from the site of application to the adjacent tissue after application. With the locally confined treatment, it can be exploited that the site where the chitosan or chitosan containing composition is applied and thus the activity takes place can be well controlled in order to achieve essentially only a local activity. Typically, a systemic activity, i.e. a medical activity in regions of the patient's body where such activity is not required and/or not desirable, can be avoided. The invention can thus reduce side effects and contribute to the swift recovery of the patient.

The locally confined treatment may be an external use of the chitosan or the chitosan containing composition. However, an internal treatment is also possible: The chitosan or the chitosan containing composition may for example be injected in a well-defined area of the patient's body, inhaled or swallowed. E.g., the chitosan or the chitosan containing composition is applied in contact with the tissue to be treated or in contact to tissue surrounding the tissue to be treated.

In one embodiment of the invention, the treatment is a topically confined treatment. "Topically confined" in the context of the present invention refers to a "locally confined" treatment, in which the application takes place on a surface of the patient's tissue, for example a part of the patient's skin. With this embodiment of the invention it can be achieved that the activity of the chitosan or the chitosan containing composition can be limited to such surface (e.g. the skin) and an area immediately beneath the surface, or less than 10 mm, or less than 5 mm beneath the surface. Exemplary surfaces include healthy biological surfaces, infected surfaces, and wounds. The surfaces may be topically accessible for example by direct application, such as by droplets, rinsing, spraying or aerosol inhalation. Surfaces may include i.a. outer surfaces, surgically generated surfaces, and surfaces of the nasal, laryngeal and pulmonary cavities, including the alveoli.

The treatment according to the invention may be for lasting prevention and/or acute treatment.

The chitosan or the chitosan containing composition according to the invention may be applied to the surface of a material, e.g. a tissue to be treated. The material or tissue to be treated may in one dimension (typically the depth dimension) be less than 10 mm, or less than 5 mm thick. In this embodiment it is exploited that the chitosan or chitosan containing composition according to the invention can be applied to a surface of such tissue and a sufficient concentration of the chitosan or chitosan component in the material or tissue can be achieved, e.g. by diffusion, to exhibit a activity.

The material may be a human or animal tissue, e.g. a healthy tissue, alveole, wound, burn, abrasion, perforation, cut or laceration.

Tissues to be treated may include chronic wounds, post-surgery wounds, cuts, abrasions, burns, razor burn, bedsore, ulcerous tissue, wounds caused by viruses which tend to become ulcerous, tissue affected by dermatoses, for example athlete's food disease, diabetic foot and psoriasis, insect bites, tissues affected by acne, in particular acne vulgaris, tissue affected by lupus erythematosus, in particular malar rash, mucosal tissue, tumor tissue, tonsils, tissue in the genital area and tissue in body cavities or orifices. The invention can also be of use when surgery is performed on a patient. When treating wound tissue, the chitosan or chitosan containing composition may be applied into or onto the wound.

Typically, the material to be treated is a hydrophilic material or a liquid such as an aqueous solution or suspension.

An aqueous suspension includes for example bacterially contaminated water to be decontaminated to be used as drinking water.

In an exemplary embodiment, the composition according to the present invention may be added as a stock solution of e.g. 3% to a final concentration of e.g. 0.1% in water to be decontaminated. Water treated in such a way can be decontaminated from bacteria such as E. coli as demonstrated experimentally even with offering such bacteria in growth medium.

By adding a chitosan containing composition according to the present invention to an aqueous medium such as water, chitosan may immediately form microdisperse droplets, e.g. as a consequence of a pH shift. This may be observable as a shift from transparency to turbid suspension of undissolved chitosan including soluble chitosan for subsequent release into the aqueous interface. Following e.g. a few hours of incubation with a composition according to the present invention water may become drinkable.

Alternatively to adding a stock solution of a chitosan containing composition according to the present invention, such stock solution can be dried and added in dried form, e.g. as a powder. Such a powder may be formed by spray drying.

Hydrophilic surfaces also include inanimated surfaces such as walls or other surfaces in buildings such as surfaces of furniture. Such surfaces can be treated by using e.g. sprays or aerosols of the chitosan containing composition according to the present invention. E.g., a 0.1% w/v or less chitosan containing spray or aerosol formed by conventional techniques may be used. Such aerosols or sprays can also be used for disinfecting or decontaminating animated material. In particular, patients having tuberculosis may be treated by administering a chitosan containing composition according to the present invention via inhalation According to one embodiment of the composition according to present invention, the chitosan has a concentration on the surface of the material of at least 0.01% w/v, optionally of at least 0.1% w/v. This may be achieved by applying such concentrations directly or by being formed as a deposit, e.g. as a consequence of evaporation of solvent. In particular, the applied chitosan will not evaporate or prevent evaporation because of its lack of hygroscopic property. Thus, solutions of lower concentrations of chitosan such as less than 0.01% w/v, optionally of less than 0.001% w/v can be applied as well, as biologically active higher concentrations may result from evaporation of solvent on such surfaces.

In some embodiments, the chitosan or the chitosan component of the chitosan containing composition exhibits a specific pharmaceutical activity for the microbial infection to be treated if the chitosan or the chitosan component has a concentration higher than 1% w/v or higher than 0.1% w/v, or higher than 0.01% w/v (weight per volume) in the site of action, e.g. the tissue to be treated. Further, the chitosan or the chitosan component of the chitosan containing composition typically exhibits no specific pharmaceutical activity for the microbial infection to be treated if the chitosan or the chitosan component has a concentration lower than 0.001% w/v (weight per volume), or lower than 0.01% w/v, or lower than 0.1% w/v. Thereby, it can be achieved that the pharmaceutical activity is locally confined to a site of action such as a tissue to be treated in which a sufficiently high concentration of the chitosan or chitosan component is maintained.

In some embodiments, the chitosan or the chitosan component of the chitosan containing pharmaceutical composition exhibits a specific pharmaceutical activity for the microbial infection to be treated if the chitosan or the chitosan component has a concentration higher than 100 µM/L (micromol per liter), or higher than 10 µM/L, or higher than 1 µM/L in the site of action, e.g. the tissue to be treated. Further, the chitosan or the chitosan component of the chitosan containing pharmaceutical composition typically exhibits no specific pharmaceutical activity for the microbial infection to be treated if the chitosan or the chitosan component has a concentration lower than 0.1 µM/L, or lower than 1 µM/L, or than 10 µM/L.

In another embodiment, the composition according to the present invention may be administered of applied in combination with another disinfecting, sanitizing or sterilizing agent.

Suitable disinfecting, sanitizing or sterilizing agents are those well known to the person skilled in the art.

Disinfectants are substances that are applied to non-living objects to destroy microorganisms that are living on the objects. Exemplary disinfectants include alcohols, aldehydes, oxidising agents, phenolics and quaternary ammonium compounds.

Sanitisers are substances that simultaneously both clean and disinfect.

Sterilization refers to any process that eliminates (removes) or kills all forms of life, including transmissible agents (such as fungi, bacteria, viruses, spore forms, etc.) present on a surface, contained in a fluid, in medication, or in a compound such as biological culture media. Sterilization can be achieved by applying the proper combinations of heat, chemicals, irradiation, high pressure, and filtration. Exemplary sterilizing agents include ethylene oxide, ozone, and hydrogen peroxide.

According to another embodiment, the pH of an aqueous chitosan solution according to the present invention may be in a range from pH 5 to pH 6, e.g. from about 5.2 to about 5.8 or about 5.5.

According to still another embodiment, the composition according to present invention, e.g. an aqueous solution, does not contain an organic solubilizer such as an alcohol.

In some embodiments, the chitosan is native chitosan. Native chitosan may be obtained by deacetylation or acetylation of fractions of chitosan derived from natural sources. In particular, the term "native chitosan", in the context of the present invention refers to the defined chemical entity chitosan, which is a poly(N-acetyl-D-glucosamine-co-D-glucosamine) copolymer or a poly(D-glucosamine) homopolymer. Any cross-linked or otherwise chemically modified chitosan is considered a chitosan derivative, having different properties than native chitosan. In the context of the present invention the term "native chitosan" includes both the chitosan base and chitosan in the form of a chitosan salt, dissolved or un-dissolved. When in the context of the present invention it is referred to "chitosan" in general, this can be any form, salt or base, of native chitosan or any derivative of a poly(N-acetyl-D-glucosamine-co-D-glucosamine) copolymer or a poly(D-glucosamine) homopolymer, cross-linked and/or otherwise modified.

The chitosan may have a degree of acetylation (DA) of 40% or less, e.g. 20% or less, or 10% or less. In specific embodiments, the chitosan has a degree of acetylation of 2% or less and, optionally, of 1.5% or less.

In some embodiments, the chitosan is deacetylated. In the context of the present invention the term "deacetylated chitosan" means that the chitosan's DA is less than 2.5%. Such low DA can contribute to the chitosan's antimicrobial activity. In an exemplary chitosan or chitosan containing composition according to the invention, the deacetylated chitosan's or the deacetylated native chitosan's DA is 2% or less, or 1.5% or less, or 1% or less, or 0.5% or less. Such extremely low degrees of acetylation can further improve the antimicrobial properties of the invention. Also, lysozymal biodegradation of the chitosan or its dissolution can be limited or prevented.

The DA can be obtained by means of $^1$H NMR spectroscopy as, e.g., disclosed in Lavertu et al., "A validated $^1$H NMR method for the determination of the degree of deacetylation of chitosan", J. Pharm. Biomed. Anal. 2003, 32, 1149. "Deacetylated native chitosan" in the context of the present invention refers to chitosan that is both native and deacetylated according to the above definitions.

The chitosan can be prepared by a method that involves at least two deacetylation steps. Two deacetylation steps are separated (and thus distinguished from a single deacetylation step) at least by a washing step in which by-products of the deacetylation, such as acetate, are at least partly removed. Typically, at least one or all deacetylation steps are hydrolysis steps. A hydrolysis step may involve mixing the chitosan with a solution of a hydroxide such as sodium hydroxide. During a hydrolysis step, the chitosan may be exposed to a temperature higher than room temperature, e.g. 100° C. At the end of each deacetylation step, the chitosan may be washed, e.g. in water. Moreover, at least at the end of the last deacetylation step, usually at the end of each deacetylation step, the chitosan is dried.

In certain embodiments of the invention, between two deacetylation steps an acetylation step may be performed. Any exemplary acetylation step may involve mixing the chitosan or acidic chitosan solution with an organic solvent, followed by treatment with a carboxylic anhydride at room temperature. At the end of the acetylation step, the acetylated chitosan may be washed and dried.

In one embodiment, the chitosan is present in two fractions with regard to their solubility at a certain pH in the sense that at this pH one chitosan fraction is insoluble while the other is soluble. Thereby, it can be achieved that at this pH the insoluble fraction can take a solid or gel-like form, e.g. that of a hydrogel, and can thus act as a reservoir or matrix holding the soluble fraction, which soluble fraction can diffuse from the reservoir or matrix into the material, e.g. the target tissue or into the patient's blood or into contaminated water.

Further, the first fraction may be a fraction of more than 10% of the chitosan in the composition. In one embodiment, the first fraction may be in a form that is insoluble at a pH of 6.5 or greater, e.g. at a pH in the physiological range such as at a pH of about 6.5 to about 8. The first fraction of the chitosan may contain polymers having a molecular weight of 10 kD or more. As already described above, the first fraction of the chitosan may be configured to form a solid or gel-like precipitate on the surface of the material or in the material.

E.g., a first fraction of more than 10% of the chitosan may be present in a form that is insoluble at least at a pH of 6.5, e.g. at least at any pH between 6.5 and 8.5. This fraction may comprise more than 20%, or more than 50% of the chitosan. E.g., the fraction is also insoluble at a pH of 6.3, or at least at any pH between 6.3 and 8.5. In this embodiment of the invention, the chitosan or the chitosan containing composition can take the form of a solid or a gel, such as a hydrogel.

Further, the second fraction may be a fraction of more than 1% of the chitosan in the composition. Further, the second fraction may be present in a form that is soluble at a pH in the physiological range such as at a pH of 6.5 to 8. Further, the second fraction of the chitosan may contain oligomers or low-molecular weight polymers having a molecular weight of less than 10 kD.

In particular, this second fraction may comprise more than 1%, or more than 5%, or more than 10% of the chitosan. E.g., the fraction is also soluble at a pH of 7.0, or also at a pH of 7.5. With this embodiment of the invention, it is achievable that said fraction of the chitosan can readily diffuse into the material to be treated.

The terms "soluble" and "dissolve" in context with chitosan includes a process of mass loss of chitosan without molecular weight decrease (i.e., without decrease in polymer chain length) due to solubility in an aqueous environment. This is to be distinguished from "degradation", which is the process of molecular weight decrease due to depolymerisation of chitosan.

Typically, the pH at which a certain chitosan is soluble depends on its chain length and therefore on its molecular weight. Moreover, typically, the chitosan or the chitosan component of the composition according to the invention contains a distribution of molecular weights. E.g., a first fraction of more than 10% of the chitosan has a molecular weight of 10 kD (kilodalton) or more. This fraction may comprises more than 20%, or more than 50% of the chitosan. In another embodiment, a second fraction of more than 0.1% of the chitosan has a molecular weight of less than 10 kD. This fraction may comprises more than 1%, or more than 5%, or more than 10% of the chitosan. E.g., the average molecular weight of this fraction is greater than 1 kD.

In some embodiments, the chitosan is part of a composition comprising other components in addition to the chitosan. However, chitosan is usually the main component of the composition. In the context of the present invention, the expression "main component" with regard to chitosan or a type of chitosan (such as chitosan in general, deacetylated chitosan, native chitosan or deacetylated native chitosan) means that the respective type of chitosan makes up at least 50% by weight of the composition. Thus, if e.g. the chitosan or chitosan containing composition material is provided as a solid or gel-like film to be applied to the tissue, this film is required to be made up of the respective type of chitosan by at least 50% by weight. In the case of the liquid chitosan containing composition, the expression "main component" with regard to the constituent(s) other than water in the aqueous mixture means that at least 50% by weight of the combination of all constituents other than water must be the respective type of chitosan.

In still another embodiment the composition is aerolisable, suspensable, sprayable and/or inhalable. In contact with an aqueous solution to be treated which has a pH of greater than e.g. 5.5 such compositions may form a suspension of droplets of solidified gel due to an induced pH shift. Such gel droplets of gel layers otherwise form upon spraying to surfaces or interfaces or exposing such surfaces or interfaces to aerosols containing said composition.

In a specific embodiment the composition may be free of alcohol. In particular, the composition may be free of alcohol or any other organic solubilizer or stabilizer. Further, the chitosan containing composition may be free of organic solvents in general, including, in addition to alcohols, esters, alkanes, halogenated solvents, amines and amides. It may, however, frequently contain an organic acid; organic acids are not considered organic solvents in the context of the present invention. Usually, the composition material comprises no additional preservative. It may be free of aseptic agents, antioxidants and surfactants, thereby reducing the risk of toxic or allergic reactions.

In some embodiments, the chitosan containing composition comprises at least one pharmaceutically active and/or bioactive constituent other than chitosan. Suitable bioactive constituents may e.g. be proteins, peptides or derivatives thereof, nucleic acids or derivatives thereof, low molecular weight compounds active as drugs, such as antibiotics or anti-inflammatory drugs, or agonists or antagonists of the innate immune system, or stimulating or differentiating growth factors for stimulating or differentiating growth of at least one sub-type of cells, or resins with affinity to certain components to be extracted from a wound surface, or dissolved or dispersed compounds or polymers with decorative functions such as light absorbing, fluorescent or phosphorescent or light reflecting particles. Alternatively, or in addition, the chitosan containing composition may comprise biological cells.

In one embodiment of the invention, the chitosan containing composition may comprise a pH-sensitive dye for visually indicating the pH at the site of application. The pH can be used as a proxy for indicating the condition of the material or tissue at the site of application. In a preferred embodiment of the invention, the composition is transparent, in particular if it is in the solid, gel-like or solidified form as explained in more detail below. In external applications of the composition this can make it easier for a physician to inspect the tissue treated, in particular if it is a wound tissue. In some embodiments, the chitosan or the chitosan containing composition is a transparent solid film. In others the composition is a mixture such as a dispersion, a suspension or a solution that forms a transparent film when applied to the tissue. Also, in the case that the composition comprises a pH-sensitive dye the colour of the dye can be judged due to the transparency of the chitosan containing composition.

Typically, the composition is a liquid. In general, after application, at least a fraction of the liquid composition will solidify, i.e. the composition will turn into a solid or a gel, for example a hydrogel. In some embodiments of the invention, removal, e.g. evaporation, of the solvent that was present in the liquid composition when it was applied causes or at least contributes to the solidification. Additionally or alternatively, solidification may be caused or contributed to by other factors such as chemical or physical cross-linking of polymeric components of the composition.

After application of the composition the concentration of the chitosan may increase due to removal, e.g. by evaporation, of other components, in particular of a solvent. Such removal may occur spontaneously, that is without requiring any further measures to be taken to initiate the concentration process such as applying additional chemicals or heat. In other words, the chitosan containing composition may be self-concentrating. To promote the self-concentration process, a chitosan material or the chitosan containing composition may be chosen that is non-hygroscopic when applied.

In some embodiments, the chitosan containing composition is an aqueous mixture, e.g. a dispersion or a suspension, e.g. a solution, i.e. it comprises water as the mixture medium or solvent, respectively. Moreover, in some embodiments of the invention it may comprise a co-solvent, for example an alcohol such as isopropanol. This can lead to faster evaporation of the solvent if a fast solidification of (a fraction) of the composition is required. Other embodiments, as discussed before, are free of alcohol, e.g. free of organic solvents in general, e.g. in order to avoid tissue irritation.

The solute or more generally the constituent(s) of the composition that remain(s) once the mixture medium is removed upon solidification of the composition may comprise or consist of a chitosan salt such as the salt of native chitosan or the salt of a chitosan derivative. Exemplary salts are those derived from the dissolution of a chitosan such as native chitosan, in an inorganic acid, such as hydrochloric acid, or an organic acid selected from the group of monobasic or multibasic organic acids having 2 to 12 carbon atoms and a first pKa value between 1 and 5, such as acetic acid, citric acid, lactic acid, malic acid, succinic acid, mandelic acid, oxalic acid, tartaric acid, ascorbic acid, etc.

Chitosan such as native chitosan may be the main component other than water of the liquid composition. E.g., at least 70% by weight of the constituent(s) of the mixture other than water is chitosan, such as native chitosan. An exemplary mixture essentially only consists of chitosan, e.g. native chitosan, and water. The mixture may be acidic.

The concentration of the chitosan in the liquid composition may be less than 15%, or less than 10%, or less than 7.5%, or less than 5% or less than 2.5%, or less than 1% by weight. The concentration of the chitosan in the liquid composition may be more than 0.1%, more or than 0.25%, or more than 0.5%, or more than 1% by weight.

For application, the liquid chitosan containing composition may be sprayed onto the tissue. The mixture medium or solvent may subsequently be allowed to evaporate to form a solid or gel-like film. Typically, the film may be between 0.1 and 50 μm thick, e.g. between 1 and 25 μm. It may have a surface area sufficient to cover the tissue to be treated such as a wound, and, optionally, also some of the surrounding tissue. Accordingly, the chitosan containing composition may be provided in or in combination with a spraying apparatus for spraying the chitosan containing composition onto the tissue of the patient. An exemplary spraying apparatus comprises a container for storing the chitosan containing composition. It may also comprise pressurized gas for expelling the chitosan containing composition. The composition can be provided in two or more liquid components that are mixed shortly before or during application of the chitosan containing composition to the tissue. In this case, the spraying apparatus may comprise several containers and/or several spraying apparatus may be provided, each containing one of the liquid components. Alternatively, the liquid chitosan containing composition may be brushed onto the tissue or applied by means of a sponge, a spatula, a pipette, or gauze. Accordingly, the composition may be provided in combination with a sponge, a brush, a spatula, a pipette or gauze for applying the chitosan containing composition or at least a constituent of the chitosan containing composition to a tissue. Further, the provision of kits comprising instructions for use and compositions according to the present invention is also contemplated.

Alternatively, the chitosan or the composition according to the invention is provided in a solid or gel-like form, for example as a hydrogel. E.g., the chitosan or the composition has the form of a film. A film may be suitable for the treatment of an extended area of a tissue, e.g. the skin. E.g., the film has a surface area sufficient to cover the tissue to be treated, such as a wound, and optionally also some of the surrounding tissue. An exemplary film has a smooth surface, e.g. with an average roughness $R_a$ of 1 μm (micrometer) or less, or 0.3 μm or less, or 0.1 μm or less. A smooth surface can reduce the formation of mechanical anchoring to the tissue to which it is applied, thereby facilitating removal of the chitosan or the composition after use. An exemplary film may be less than 10 mm thick, or less than 1 mm. Typically, the film when dry is between 0.5 and 500 µm thick, or between 5 and 100 µm, or between 10 and 50 µm, or between 20 and 30 µm. Alternatively, the solid or gel-like chitosan or chitosan containing composition may have the shape of a fiber or a tube. A typical fiber or tube is between 10 µm and 10 mm (millimeters) in thickness and between 1 mm and 100 cm (centimeters) in length.

E.g., at least 70%, or at least 90%, or at least 95% by weight of the solid or gel-like composition is chitosan, e.g. native chitosan.

An exemplary solid or gel-like chitosan or composition comprising chitosan is at least partly water-soluble. In other words, at the time it is provided for being applied to the material such as a patent's tissue it can be dissolved at least partly in water at neutral pH. The chitosan may for example be a chitosan salt, e.g. the salt of native chitosan or a chitosan derivative. The chitosan or chitosan containing composition may adhere well to the material. Thereby, it can be avoided that chitosan or the chitosan containing composition prematurely detaches from the material. This embodiment of the invention exploits the fact that chitosan salt is soluble in an aqueous solvent of neutral pH. Thus, wet or pre-wetted tissue can liquefy the surface of the chitosan or chitosan containing composition, providing for a durable contact with the material. Preferred salts are those derived from the dissolution of a chitosan such as native chitosan, in an inorganic acid, such as hydrochloric acid, or an organic acid selected from the group of monobasic or multibasic organic acids having 2 to 12 carbon atoms and a first pKa value between 1 and 5, such as acetic acid, citric acid, lactic acid, malic acid, succinic acid, mandelic acid, oxalic acid, tartaric acid, ascorbic acid, etc. In an alternative embodiment of the invention the chitosan is present in the form of the chitosan base.

E.g., a chitosan salt, or a salt of native chitosan, makes up the main component of the solid or gel-like chitosan containing composition. E.g., at least 70%, or at least 90%, or at least 95% by weight of the solid or gel-like chitosan containing composition is a chitosan salt, or a salt of native chitosan.

After the liquid chitosan containing chitosan containing composition or the solid or gel-like water soluble chitosan or chitosan containing composition is applied, and in the case of a liquid composition during or after solidification, it may be allowed to transform into a water-insoluble form, e.g. a chitosan base. This transformation may, for example, occur due to evaporation of a constituent of the chitosan containing composition upon contact with air. It may also be a result of an interaction of the chitosan with a material, e.g. body fluid and/or the tissue itself; for example the relatively high pH of blood and/or the attachment of proteins present in the blood to the chitosan may induce the transformation. Alternatively or additionally, transformation may be achieved by applying a transformation medium, e.g. an aqueous alkaline solution, to the chitosan or chitosan containing composition. It can be achieved that after transformation the chitosan or chitosan containing composition remains in place and therefore pharmaceutically or biologically active under normal condition, e.g. when the tissue is cleaned under tap water (neutral pH) or when soap (alkaline) is applied. The chitosan or composition comprising chitosan can be provided in combination with the transformation medium as a kit.

In one embodiment of the invention, the chitosan or the chitosan containing composition has a pH below 8.5, or below 8, or around 7 to 7.5. An exemplary pH is above 6.3, or above 6.5. According to this embodiment of the invention one fraction of the chitosan can be soluble and the other insoluble, acting as a reservoir or matrix for the soluble fraction. Also, the pH is close to that of healthy tissue, thereby avoiding irritation or damage of the tissue to which the chitosan containing composition is applied.

In another embodiment of the invention, the chitosan or the chitosan containing composition has a pH of below 6.3, or below 6, or around 5 to 5.5. An exemplary pH is above 3.0, or above 4.0, or above 4.5. Up to a pH of 6.3 chitosan is in general soluble in an aqueous medium. This embodiment of the invention applies to external applications of the chitosan or chitosan containing composition. According to this embodiment of the invention the pH is close to that of the surface of healthy skin, thereby avoiding irritation or damage of the tissue to which the chitosan or chitosan composition is attached. Moreover, due to subsequent transformation, the pH may rise above 6.3, or above 6.5, so that that one fraction of the chitosan can remain soluble while the other turns insoluble, acting as a reservoir or matrix for the soluble fraction.

It has further been found that the presence of glycerol in the solid chitosan or chitosan containing composition can accelerate the transformation from a water-soluble state into a state in which the product is only soluble in an acid liquid solvent. For example, in the case of a native chitosan salt as a chitosan salt, transformation can be accelerated from approximately one month to one week. Without limiting the invention to a specific theory, it is believed that the acceleration may be due to the glycerol's effect of disrupting the crystalline structure of the chitosan salt. The faster transformation may allow the transformation to set in earlier. The glycerol content can make up at least 10%, or at least 15%, or at least 20% by weight of the solid composition's chitosan salt content by weight. The glycerol may be present at a concentration of more than 10%, or more than 15%, or more than 20% by weight. The glycerol may be present at a concentration of less than 60%, or less than 45%, or less than 30% by weight.

The chitosan or the composition comprising chitosan according to the invention may be provided as a kit in combination with a detachment solvent to facilitate detachment of the water-insoluble solid or gel-like chitosan or the chitosan containing composition from a patient's tissue after use, e.g. to be replaced or at the end of a therapy. In the context of the present invention, a "detachment solvent" is a liquid that can be applied to the chitosan or the chitosan containing composition when it is in a solid or gel-like state and that can facilitate detachment of the product from the tissue, e.g. by at least partly dissolving and/or swelling it. An exemplary detachment solvent can reduce the adherence of the product to the patient's tissue. Thus, with the detachment solvent it can be avoided that the tissue is damaged during removal of the chitosan or the chitosan containing composition, and in particular it can be avoided that when the chitosan or chitosan containing composition is removed, parts of the tissue beneath it that adhere to the chitosan or the pharmaceutical composition are torn away. Amongst other cases, this can be of advantage where the chitosan or the chitosan containing composition is applied to a wound as a wound dressing or as part of a wound dressing, because wound tissue can be very sensitive to mechanical stress. By providing the chitosan or the chitosan containing composition together with the detachment solvent in a kit it can improve compliance in the sense that the patient is less likely to attempt to separate the chitosan or chitosan containing composition from the tissue without previous application of the detachment solvent. The kit according to the invention can also prevent the user from applying another, unsuitable or possibly even harmful solvent.

E.g., the detachment solvent is an aqueous solvent, e.g. distilled water, an aqueous solution of ionic compounds, such as an aqueous sodium chloride solution, a buffered solution, such as an acetic acid/acetate buffered solution, or an aqueous solution of non-ionic compounds, such as an aqueous glucose solution. Water as a solvent is less irritating to the skin than many organic solvents. While in principle, the aqueous detachment solvent according to the invention may in addition to water comprise one or more co-solvents other than water, e.g. an organic co-solvent such as isopropanol or another alcohol, an exemplary detachment solvent is free of organic solvents, including alcohols, esters, alkanes, halogenated solvents, amines and amides. It may, however, frequently contain an organic acid; organic acids are not considered organic solvents in the context of the present invention.

The detachment solvent can be acidic. This embodiment of the invention exploits the fact that the solubility of chitosan can be pH-dependent. Thus, advantageously, the pH of the detachment solvent can be selected from a range in which all chitosan fractions dissolve. An exemplary pH of the detachment solvent is below 6.5, or below 6.3. E.g., the pH of the detachment solvent is below 6, or below 5.5, or below 5. The pH of the detachment solvent may be above 3.5. Thereby, irritation of the tissue due to high acidity of the detachment solvent can be avoided. E.g., the pH of the detachment solvent is above 4, or above 4.5. An exemplary detachment solvent comprises a surfactant, e.g. a polysorbate such as Tween. Alternatively or in addition it may comprise substituted or unsubstituted polyalkyleneoxide, such as polyethylene glycol or polypropylene glycol esters. It has been found that the presence of such additives can considerably facilitate detachment of the solid, gel-like or solidified liquid chitosan or chitosan containing composition.

The amount of detachment solvent provided in the kit is at least 5 times per weight, or at least 50 times per weight of the amount of the chitosan provided in the kit. By providing a sufficient amount of detachment solvent, it can be avoided that the pH of the chitosan or the chitosan containing composition falls under a certain threshold. For application, the detachment solvent may be sprayed or brushed or applied by means of a sponge, a spatula, a pipette or gauze. Accordingly, a preferred kit contains a sponge, a brush, a spatula, a pipette or gauze for applying the detachment solvent. The detachment solvent may for example be provided in a sealed bottle or a disposable pipette, or by means of gauze, a sponge or a gel soaked with the detachment solvent. It may also be provided in a spraying apparatus. The preferred spraying apparatus comprises a container for storing the detachment solvent. It may also comprise pressurized gas for expelling the detachment solvent.

An exemplary kit according to the invention comprises both a solid or gel-like chitosan or composition comprising chitosan and a liquid composition comprising chitosan. In an exemplary method according to the invention, first the liquid and subsequently the solid or gel-like chitosan of chitosan containing composition is applied. E.g., in this method, the solid or gel-like product is applied before the product has solidified. It has been found that the liquid product can facilitate attachment of the solid or gel-like product to the target tissue. This may apply e.g. to water-soluble solid or gel-like chitosans or compositions comprising chitosan and as compared to an alternative method in which the water-soluble solid or gel-like chitosan or chitosan containing composition is wetted with water before attachment. This is because the latter method has been found to frequently lead to an undesirable deformation of the solid or gel-like chitosan or chitosan containing composition, which deformation can be avoided by the application of the liquid chitosan containing composition for attachment of the solid or gel-like chitosan or chitosan containing composition. E.g., in the kit, the liquid composition is one exemplary liquid chitosan containing compositions described herein. Similarly, the solid or gel-like chitosan or composition comprising chitosan is one of the exemplary solid or gel-like chitosans or chitosan containing compositions described herein. E.g., the liquid compositions and/or the solid or gel-like chitosan or chitosan containing composition and the detachment solvent are provided in separate containers.

The chitosan or pharmaceutical composition comprising chitosan according to the invention may be applied as a tissue dressing, e.g. a wound dressing, or it may form part of a tissue dressing or wound dressing. Similarly, the tissue dressing material according to the invention may be part of a tissue dressing comprising other components. In one embodiment of the invention, the chitosan or the chitosan containing composition may be part of a tissue dressing that comprises a first layer, which layer is formed of the chitosan or composition, and at least another layer formed of another material, this other layer acting as a support. In particular, the support can help preventing premature detachment of the tissue dressing from the tissue. The support may be located at the side of the tissue dressing opposite to the side that is in contact with the tissue. E.g., the support is adjacent to the chitosan or chitosan containing composition. The support according to the invention may be advantageous if the respective type of chitosan, e.g. deacetylated native chitosan, is provided in the tissue dressing material in the form of the chitosan base, as the chitosan base in general adheres less well to tissue than a chitosan salt containing tissue dressing material. The support may for example be a woven fabric, foam or a perforated film. The support may for example be of natural materials such as cotton or a natural or synthetic polymer. Suitable polymers include biodegradable polymers, such as polyesters, polyorthoesters, polycarbonates, polyanhydrides, polyurethanes, polyphosphazenes, polyphosphoesters, polysaccharides, polypeptides, as well as derivatives, copolymers, and blends based on these polymers. Suitable polymers also include biodissolvable polymers, such as polyvinyl alcohol, polyvinyl acetate, poly-N-vinyl pyrrolidone, polyethylene glycol, polypropylene glycol, polysaccharides, polypeptides, as well as derivatives, copolymers, and blends based on these polymers. Furthermore, the support may consist of a non-biodegradable/non-biodissolvable polymer, such as silicones, polyurethanes, polyethylene terephthalate, polytetrafluorethylene, polysulfones, polyethersulfones, polyether ether ketones, polycarbonates, polymethacrylates, polysaccharides, polypeptides, as well as derivatives, copolymers, and blends based on these polymers.

An exemplary tissue dressing according to the invention may comprise a first layer, which layer is formed of the chitosan or chitosan containing composition, and another layer formed of another material, this other layer acting as an at least partial moisture barrier. In other words the other layer can prevent or at least delay the evaporation of water during treatment of the tissue with the tissue dressing according to the invention. This can be of advantage when the tissue dressing is applied to dry wounds. The other layer may be located at the side of the layer of the tissue dressing opposite to the side that is in contact with the tissue. E.g., the other layer is adjacent to the chitosan or chitosan containing composition. The invention also encompasses tissue dressings that have both a support layer and another layer that acts as an at least partial moisture barrier. Both functions, that of a support and that of an at least partial moisture barrier, can also be fulfilled by a single other layer. The other layer may for example be of silicone or another polymer or polymer composition from the groups of polymers listed above. Typically the other layer is between 10 and 1000 µm thick, or between 50 and 500 µm. In some embodiments of the invention, the other layer is perforated. The holes of the perforation typically are between 10 and 1500 µm in diameter, or between 50 and 1000 µm. In an alternative embodiment of the invention, instead of the moisture barrier a layer is provided that can take up fluid, e.g. wound exudate. A suitable material may for example be polysaccharide-based hydrogels or hydrocolloids including cellulose derivatives, or polyurethane foams. This can be of particular advantage when the tissue dressing is applied to wet wounds.

In one embodiment of the invention, the chitosan or chitosan containing composition, e.g. the tissue dressing, is provided in a container that can prevent transformation of the chitosan or chitosan containing composition from its liquid or water-soluble state to its water-insoluble state as long as it is in the container and the shelve life has not yet expired. E.g., the container is vapour proof, or it is essentially airtight. Moreover, in some embodiments of the invention, the chitosan or chitosan containing composition on its side which is intended to be applied in contact with the patient's tissue is covered with a strippable cover sheet. The cover sheet is vapour proof, or air-impermeable. This can contribute to preventing premature transformation of the chitosan or chitosan containing composition from its liquid of water-soluble state to its water-insoluble state before it is applied to the patient's tissue.

An exemplary chitosan or chitosan containing composition has a water uptake capacity of less than 1500% by weight, or less than 100%, or less than 80%. Thereby it is achievable that a degree of humidity that is favourable for wound healing can be maintained under the tissue dressing as applied to a wound site. E.g., the chitosan or chitosan containing composition in a solid or gel-like form has a water-uptake capacity of more than 25%, or more than 50%. This embodiment of the invention is suitable for absorbing exudative fluids and toxants. In a specific embodiment of the invention, the water-uptake capacity of the chitosan or chitosan containing composition is between 65 and 75%.

The surprising biological results observed by the present invention may be obtained by establishing an interface of highly concentrated chitosan compounds of a molecular weight such as at least 1 kDa to be concentrated at and in the interface as a consequence of being released over time from a hydrated but insoluble chitosan deposit of identical chemical nature. In this respect, a concentration gradient may be formed in a region of the material in contact with the insoluble chitosan fraction thereby setting up an interface characterized by a concentration of at least one bioactive and soluble chitosan fraction, which alone or in cooperation with other bioactive compounds of identical biological activity is able to exercise its biological effect. Such biological effect may be limited to concentrations of at least 1 µM or at least 0.01% w/v (weight per volume).

While the above invention has been described with respect to some of its embodiments, this is in no way to limit the scope of the invention. The person skilled in the art is clearly aware of further embodiments and alterations to the previously described embodiments that are still within the scope of the present invention.

Examples 1. 1H NMR Spectroscopy

Figure 1:
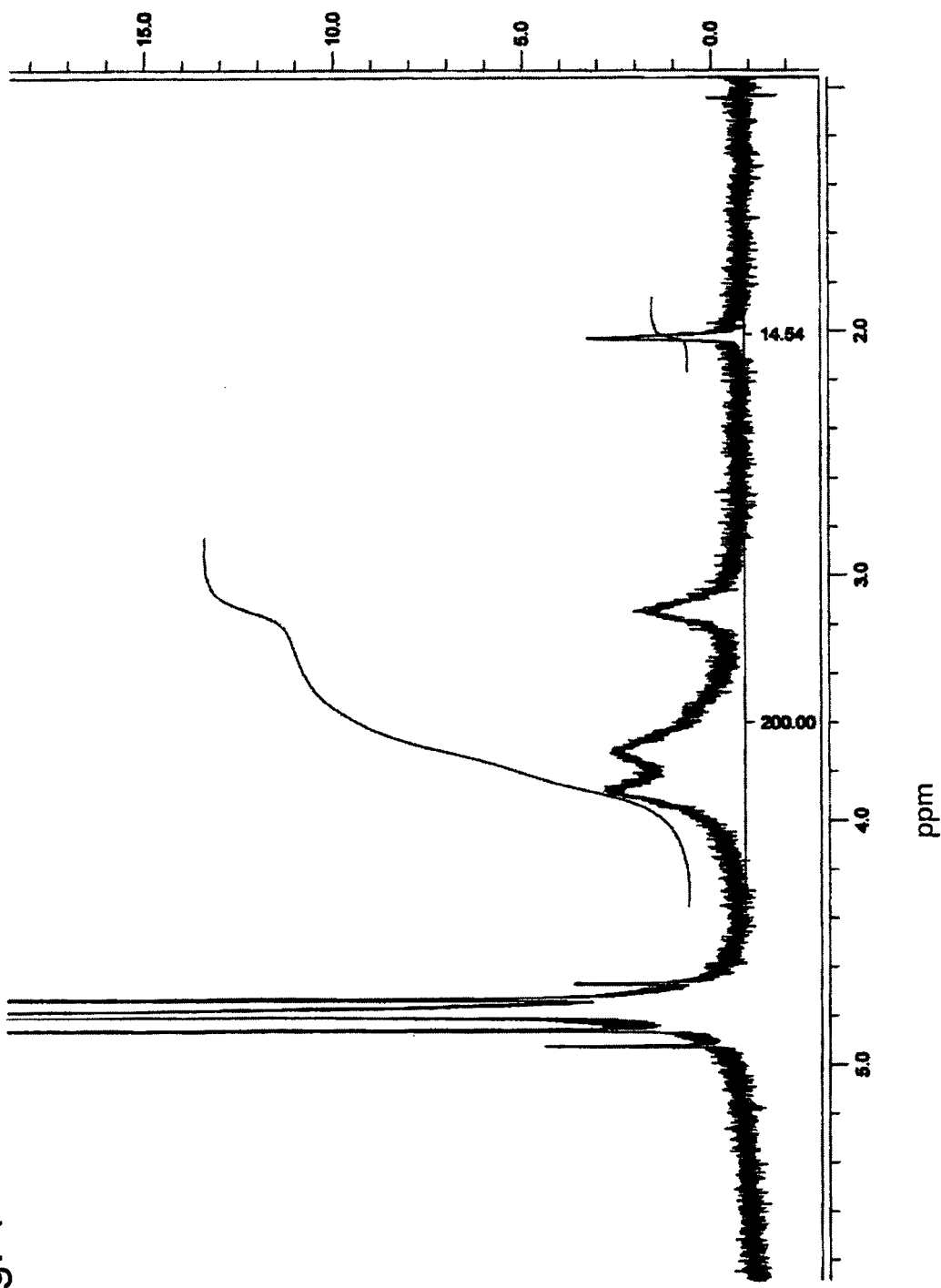
FIG. 1 shows an $^1$H NMR spectrum of native chitosan as purchased.
Figure 2:
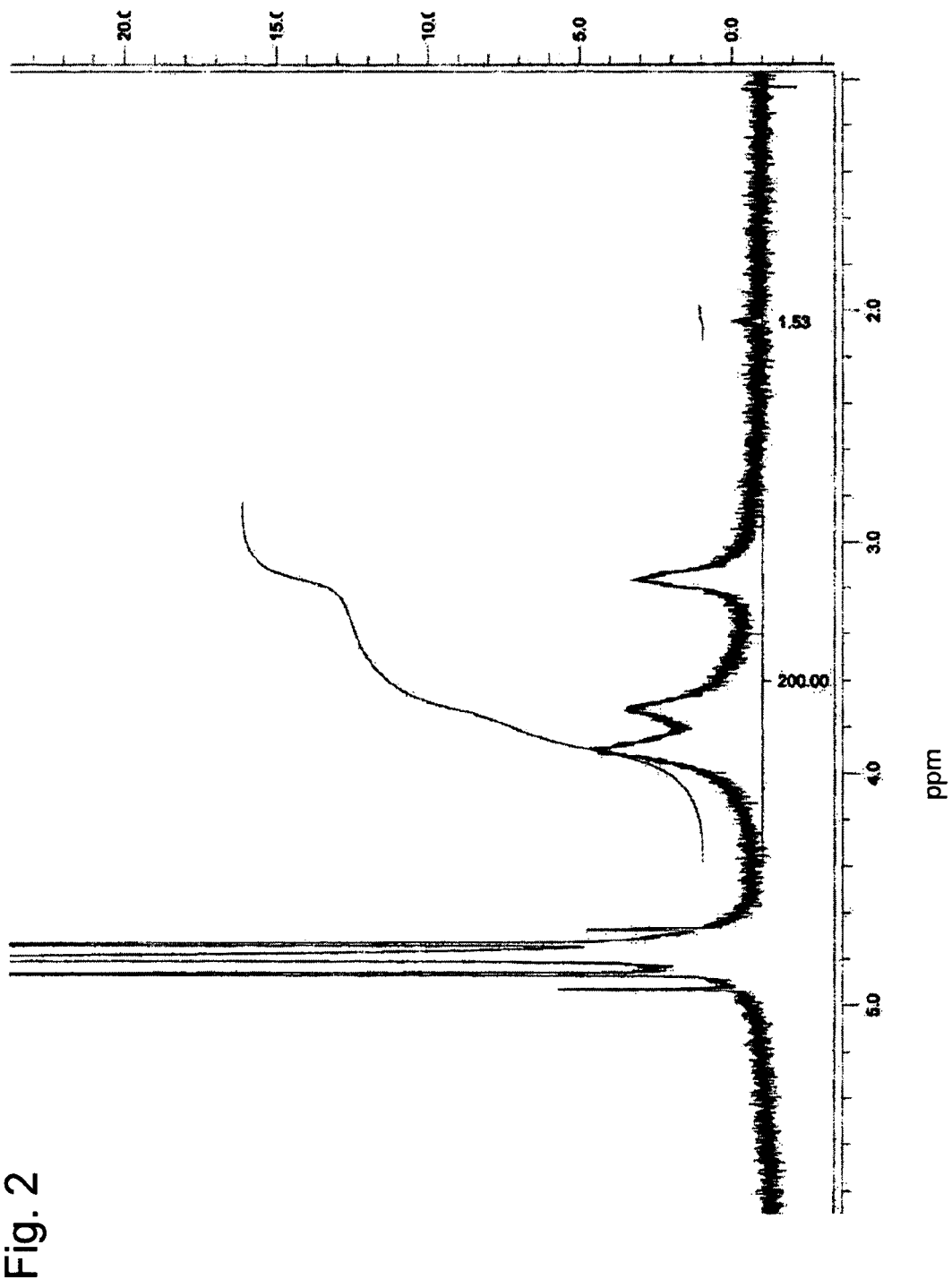
FIG. 2 shows an $^1$H NMR spectrum of native chitosan essentially deacetylated after further hydrolysis steps.

The chitosan used in the examples below was obtained in the form of fine flakes from Cognis (Germany). The degree of acetylation (DA) was determined by 1H NMR spectroscopy. FIG. 1 shows an 1H NMR spectrum obtained from this commercially available chitosan. FIG. 2 shows a corresponding 1H NMR spectrum obtained from chitosan deacetylated after further hydrolysis steps applied to the commercial product as described further below. In both cases, chitosan was analyzed in a mixture of 0.25% DCl in D2O at a chitosan concentration of approximately 0.5% (w/v). The spectra were recorded using a Bruker AC200 spectrometer. NMR chemical shifts ($\delta$, in ppm) were referenced to the signal of HDO ($\delta$=4.8 ppm). The DA, calculated by comparing the integrated area under the peaks associated with H2-H6 of the D-glucosamine subunit with that of the methyl group, was determined as 14.5% for the native chitosan as purchased, and 1.5% for the deacetylated native chitosan.

2. Synthesis of Low-DA Chitosan

For further hydrolysis, 50 g (grams) of the chitosan flakes as obtained from the supplier Cognis were placed in a glass container, and 500 g of a 45% aqueous sodium hydroxide solution were added. The glass container was well shaken to mix the components, and placed in an oven for 2 hours at 100° C. It was then removed from the oven, and 500 mL (milliliters) of distilled water were added. The mixture was filtered through a glass frit. Then, the chitosan was washed with distilled water until the pH of the filtrate reached 6.5, and dried at 100° C. for 4 h (hours). This hydrolysis treatment was then repeated, resulting in 42 g of deacetylated native chitosan having a degree of acetylation of 1.5% as determined by 1H NMR spectroscopy.

3. Preparation of Chitosan Solutions (Solutions A1, A2 and A3)

15 g of the thus obtained native chitosan having a DA of 1.5% were dissolved in 500 mL of a 2% aqueous acetic acid by gently shaking for 24 h. Below, the material is referred to as chitosan solution A1.

A second chitosan solution with a chitosan concentration of 1.5% was obtained by addition of 500 ml of distilled water to 500 ml of solution A1. Below, the material is referred to as chitosan solution A2.

A third chitosan solution with a chitosan concentration of 0.75% was obtained by addition of 1500 ml of distilled water to 500 ml of solution A1. Below, the material is referred to as chitosan solution A3.

4. Preparation of a First Example of a Solid Film-Type Chitosan (Chitosan B)

Two portions of 144 mL each of solution A2 were poured into two square-shaped moulds, 24×24 cm$^2$ (square centimeters) in size, and left in a dust-free environment for drying at room temperature. The resulting film was removed from the first mould, and sterilized using a 10 kGy (kilogray)

electron beam. An approximately 80 µm thick transparent film essentially consisting entirely of deacetylated native chitosan acetate salt was obtained. Below, the material is referred to as chitosan B.

5. Preparation of a Second Example of a Solid Film-Type Chitosan (Chitosan C)

The dried film from the second mould was placed for 2 hours in a bath containing a solution of 1.5% ammonia in methanol/water 90/10 (v/v). The film was then removed from the bath and dried by storage at room temperature. The film was sterilized using a 10 kGy electron beam. An approximately 80 µm thick transparent film essentially consisting entirely of deacetylated native chitosan base was obtained. Below, the material is referred to as chitosan C.

6. Preparation of a Third Example of a Solid Film-Type Chitosan (Chitosan D1)

144 mL of solution A2 was filtered first through a glass fiber filter (pore size approximately 1 µm), and then through a 0.22 µm filter for sterilization, poured into a square-shaped mould, 24×24 $cm^2$ in size, and left in a dust-free environment for drying at room temperature. After 3 days of storage, the resulting film was removed from the mould, transferred in a plastic bag that was then tightly sealed, and sterilized using a 25 kGy (kilogray) electron beam. An approximately 80 µm thick transparent film essentially consisting entirely of deacetylated chitosan acetate salt was obtained. Below, the material is referred to as chitosan D1.

7. Preparation of a Fourth Example of a Solid Film-Type Chitosan (Chitosan D2)

In a slightly modified procedure, 4% (w/w) glycerol was added to the filtered solution of the previous example before pouring it into the square-shaped mould. Subsequent treatment as described above for chitosan D1 resulted in a transparent film essentially consisting entirely of a mixture of deacetylated chitosan acetate salt and glycerol. Below, the material is referred to chitosan D2.

8. Preparation of a Fifth Example of a Solid Film-Type Chitosan (Chitosan D3)

In a further modified procedure, the glycerol containing solution of deacetylated chitosan was poured into a square-shaped mould which was covered with a two-layered film consisting of polyurethane/polyethylene (Platilon U073 PE, Epurex, Bomlitz/Germany), with the polyurethane side up and the polyethylene side fixed to the bottom of the mould. Subsequent treatment as described above for chitosan D1 resulted in a transparent film essentially consisting entirely of a mixture of deacetylated chitosan acetate salt and glycerol which was attached to the polyurethane/polyethylene support film. Below, the material is referred to as chitosan D3. Upon use, the polyethylene layer is removed. The remaining polyurethane layer is gas-permeable.

9. Preparation of a Sixth Example of a Solid Film-Type Chitosan (Chitosan D4)

In a slightly modified procedure to the preparation of chitosan film D2, 1% (w/w) glycerol was added to the filtered solution before pouring it into the square-shaped mould. Subsequent treatment as described above for chitosan D1 resulted in a transparent film essentially consisting entirely of a mixture of deacetylated chitosan acetate salt and glycerol. Below, the material is referred to chitosan D4.

10. Preparation of Two Examples of Chitosan with Higher DA (Chitosans E1 and F1)

Two further examples of chitosan were produced by the procedure leading to chitosan D1 with the only modification that in one case the hydrolysis step was shortened, leading to a DA of 4% (chitosan E1), and in the other case the hydrolysis step was entirely omitted, leading to a DA of 16% (chitosan F1).

11. Inhibition of *Escherichia coli* Growth on Agar

Figure 3:
FIG. 3 illustrates the effect of a chitosan solution according to the invention on *Escherichia coli* cultivated on an agar plate after 12 hours of incubation.

An agar plate was coated with 200 µL of a suspension (appr. $10^8$ cells per ml) of the gram-positive bacterium *Escherichia coli*. A circular cavity was made in the plate and 100 µL, of solution A1 was pipetted into the cavity. The plate was then incubated at 37° C. for 12 hours. The result of the experiment is shown in FIG. 3. A clear circular inhibition zone can be seen around the hole that contains the chitosan solution, indicating antibiotic activity of the chitosan solution against *Escherichia coli*.

12. Inhibition of *Staphylococcus carnosus* Growth on Agar

Figure 4:
FIG. 4 illustrates the effect of a chitosan solution according to the invention on *Staphylococcus carnosus* cultivated on an agar plate after 12 hours of incubation.

The above experiment was repeated with the gram-negative bacterium *Staphylococcus carnosus*. An agar plate was coated with 200 µL of a suspension (appr. $10^8$ cells per ml) of the bacterium and the solution A was pipetted into a cavity in the plate. The plate was then incubated at 37° C. for 12 hours. The result of the experiment is shown in FIG. 4. A clear circular inhibition zone can be seen around the hole that contains the chitosan solution, indicating antibiotic activity of the chitosan solution against *Staphylococcus carnosus*.

13. Inhibition of *Escherichia coli* Growth in Liquid Medium

Figure 5:
FIG. 5 shows centrifuge tubes with samples of a Tryptic Soy Broth medium containing a chitosan preparation according to the invention (A) and free of chitosan (B)

In order to test the antibiotic activity of the chitosan preparation according to the invention, 5 mL of solution A1 was inoculated with 100 µL of overnight activated *E. coli* (optical cell density $OD_{500}$=5) at room temperature in a Tryptic Soy Broth liquid medium. The sample was filled in a centrifuge tube and is shown in FIG. 5 on the left (sample A). For comparison, 5 mL of TSB medium free of chitosan was inoculated with 100 µL of overnight activated *E. coli* (optical cell density $OD_{500}$=5). A centrifuge tube filled with the chitosan-fee sample is shown on the right in FIG. 5 (sample B). The inoculation was followed by 16 hours of incubation at room temperature under shaking.

Figure 6:
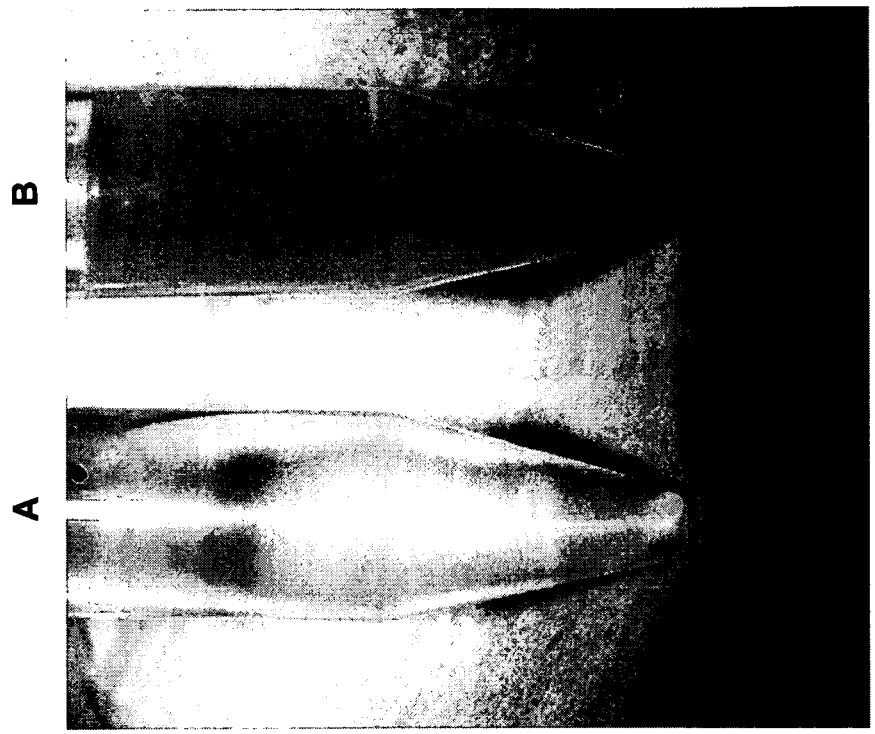
FIG. 6 shows the samples of FIG. 5 after 16 hours of incubation following the inoculation with *Escherichia coli*.

The result of the experiment is shown in FIG. 6. In the medium without chitosan (sample B), a considerable increase in the turbidity of the solution was observed, indicating bacteria growth. In contrast, the chitosan containing solution (sample A) shows no discernable increase in the turbidity. The experiment thus indicates antibiotic activity of the chitosan solution against *Escherichia coli* in the Tryptic Soy Broth liquid medium.

14. Inhibition of *Escherichia coli* Growth in Liquid Medium

In another experiment to test the antibiotic activity of the chitosan preparation according to the invention, solution A1 was inoculated with E. coli K 12 (OD 0.2) in a lysogene broth medium for 15 hours at 37 deg C. under shaking. Solution A1 was added in different volumes to yield final chitosan concentrations as specified in Table 1.

The results of this experiment are summarized in Table 1

TABLE 1

| | Chitosan concentration | | | | Control |
|---|---|---|---|---|---|
| | 0.75% | 0.3% | 0.1% | 0.03% | 0.01% | (no chitosan) |
| Observation | − | − | − | + | ++ | +++ |

− no growth; +, ++, +++ growth in increasing order

The addition of 0.1% Chitosan to E. coli in exponential growth phase starting with an OD of 0.2 for 15 h at 37° C. and shaking (in E. coli optimal growth media) led to a clearing of the solution, the solution remained sterile for an additional observation period of 5 days (RT without shaking).

15. Efficacy of Antimicrobial Preservation

The efficacy of antimicrobial preservation was tested according to the norm as described in the Ph. Eur. 7th Edition, Chapter 5.1.3, with solution A3. Two containers were each filled with 20 mL of solution A3 and inoculated with a suspension of either Pseudomonas aeruginosa ATCC 9027 or Staphylococcus aureus ATCC 6538 to give an inoculum of $10^5$ to $10^6$ microorganisms per mL. The suspension was mixed thoroughly to ensure homogeneous distribution. The inoculated product was maintained at 20° C. to 25° C. under protection from light. A 1 mL sample was removed from each container at zero hour and at the intervals specified in Table 2, and the number of viable microorganisms determined by plate count.

TABLE 2

| | CFU per ml of sample | | | | |
|---|---|---|---|---|---|
| Bacteria | 0 h | 2 d | 7 d | 14 d | 28 d |
| Pseudomonas aeruginosa ATCC 9027 | $8.6 \times 10^5$ | <10 | <10 | <10 | <10 |
| Staphylococus aureus ATCC 6538 | $9.2 \times 10^5$ | <10 | <10 | <10 | <10 |

16. Antibiotic Activity of Chitosan Fibers

To demonstrate the antibiotic activity of chitosan fibers, a chitosan fiber was produced by extrusion of 50 mL of a solution of 4% chitosan in 2% acetic acid, mixed with an equal amount of N-methylpyrrolidone (NMP) through a needle of 50 mm in length and an inner diameter of 1.0 mm. The needle was dipped into a coagulation bath containing a mixture of 2 L (liters) of NMP and 3 mL of 25% aqueous ammonia solution. After completion of the extrusion, the fiber was left in the coagulation bath over night. It was then washed twice in distilled water containing 0.1% by weight of a 25% aqueous ammonia solution for 2 hours, and then dried at room temperature.

Staphylococcus carnosus was cultured over night at room temperature in a Tryptic Soy Broth growth medium. Subsequently, 500 μL of the thus obtained bacteria suspension was used to coat a Mueller-Hinton Agar plate at pH 5.5. A chitosan fiber section of 4 centimeters in length and 0.2 millimeters in diameter was placed on the plate and incubated over night at 37° C.

Figure 7:
FIG. 7 illustrates the effect of a chitosan fiber according to the invention on *Staphylococcus carnosus* cultivated on an agar plate after overnight incubation.

The result of the experiment is shown in FIG. 7. A clear inhibition zone around the chitosan fiber was observed, indication antibiotic activity of the fiber against Staphylococcus carnosus.

17. Treatment of a MRSA Infection

A 39 year old male patient who suffers from cerebro-orbito-facial arterio-venous malformation associated with recurrent severe bleeding from facial wounds was diagnosed with MRSA wound infection. He was treated by spraying chitosan solution A3 daily for 3 weeks onto the facial wounds. After the treatment MRSA viable microorganisms could not be detected anymore and no other microbial infection could be found at the site of the chitosan treatment.

18. Water Uptake of Chitosan C

Chitosan C, produced as described in the above example, was weighted, and then placed in distilled water for 15 min. The weight of the wet film was compared to the weight of the dry film, and the water uptake was determined to be 72% by weight.

19. Water Uptake of Chitosan D4

Chitosan D4, produced as described in the above example, was weighted, and then placed in distilled water for 60 min. The weight of the wet film was compared to the weight of the dry film, and the water uptake was determined to be 1217% by weight 7 days after film preparation, and 475% by weight 14 days after film preparation.

20. Dissolution of Chitosan

Controlled dissolution of chitosans B and C was tested in dissolution experiments using distilled water, 0.9% aqueous sodium chloride solution, and 0.5% acetic acid/acetate buffered solution, respectively. The pH of the solutions was adjusted to the values indicated in Table 2 using appropriate amounts of 1 N hydrochloric acid or sodium hydroxide solutions. Chitosans B and C were cut into rectangular samples having dry weights between 5 and 10 mg each. A gauze soaked with a 100-fold per volume excess of the respective solution to the dry weight of the film was applied to each sample film and the time for complete film dissolution was recorded.

TABLE 3

| pH of the dissolution mixture | Material B (distilled water) | Material B (0.9% aqueous sodium chloride) | Material C (0.9% aqueous sodium chloride) | Material C (0.5% acetic acid/acetate buffer) |
|---|---|---|---|---|
| 4.0 | n.a. | n.a. | n.d. | 0.5 h |
| 4.5 | n.a. | n.a. | n.d. | 0.5 h |
| 5.0 | n.a. | n.a. | n.d. | 2 h |
| 5.5 | 0.1 h | 0.5 h | n.d. | 4 h | n.a. = not analyzed
n.d. = no dissolution observed after 24 h

Figure 8:
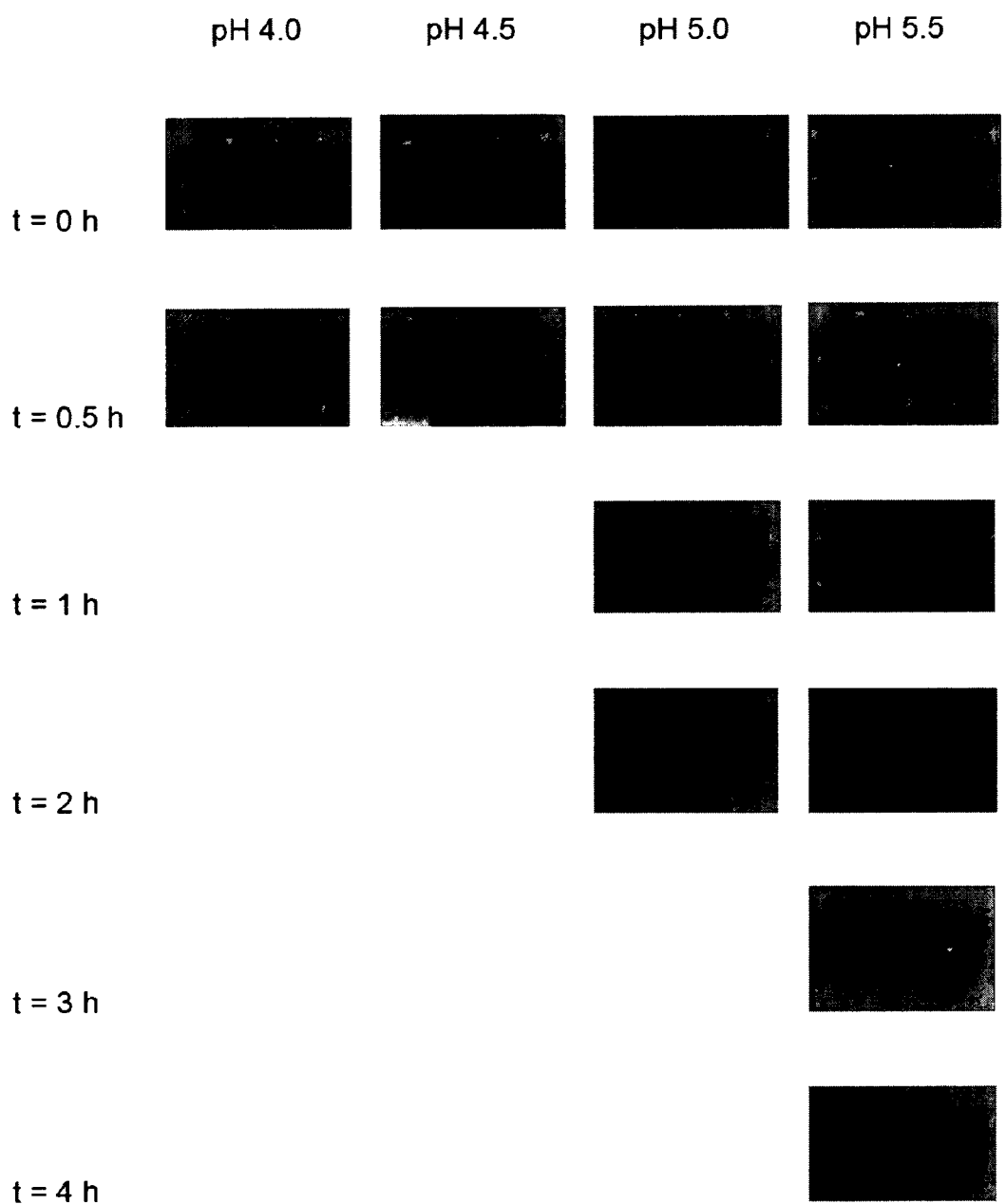
FIG. 8 illustrates the controlled dissolution of a chitosan according to the invention by applying gauze soaked with acetate buffered solution.

The controlled dissolution experiment with chitosan material C and a mixture of 0.5% acetic acid/sodium acetate (right column in Table 3), is illustrated in FIG. 8. The material has been stained by storage in 0.01% aqueous indigocarmine solution for 1 hour for better visualization. Complete dissolution was observed after 30 minutes at pH 4.0 and 4.5, after 2 hours at pH 5.0, and after 4 hours at pH 5.5, respectively.

21. In Situ Conversion of Water-Soluble Chitosan into Water-Insoluble Chitosan Samples of solution A2 and chitosans D1, D2, D3 and D4 were left unsealed on air at room temperature and a humidity of 20-40%. Under these conditions, solution A2 was drying to a solid film within several hours. Complete dissolution in distilled water was analyzed at days 3, 7, and 14. Results are summarized in Table 4.

TABLE 4

| Chitosan | Day 3 | Day 7 | Day 14 |
|---|---|---|---|
| A2 | soluble | insoluble | insoluble |
| D1 | soluble | soluble | insoluble |
| D2 | soluble | insoluble | insoluble |
| D3 | soluble | insoluble | insoluble |
| D4 | soluble | insoluble | insoluble |

Similarly, conversion of the water-soluble into the water-insoluble form of dried solution A2 and chitosans D1, D2, D3 and D4 was observed after application of the wound dressing on human skin. In the case of D3, the chitosan was applied to the skin with its chitosan side. Conversion of the water-soluble into the water-insoluble form dried solution A2 and chitosans D1, D2, D3 and D4 was also observed after alkaline treatment or storage in an alkaline atmosphere.

22. Dissolution of Chitosan with Detachment Solvent

Chitosans D1, E1 and F1 were dissolved by storage in a 2% acetic acid/acetate buffered solution. The pH of the storing solutions was adjusted to the values indicated in Table 5 using appropriate amounts of 10% sodium hydroxide solutions. Films D1, E1 and F1 made from chitosans with different degrees of acetylation (DA) were left on air for 14 days for conversion into the water-insoluble form, cut into rectangular samples of 1×1 cm² size and stored in approximately 10 mL of the respective solution, and the time for complete film dissolution was recorded.

TABLE 5

| pH | DA = 16% | DA = 4% | DA = 1.5% |
|---|---|---|---|
|  | Time for complete dissolution (min) | | |
| 4.0 | 5 | 10 | 1 |
| 4.5 | 15 | 15 | 2 |
| 5.0 | 30 | 15 | 15 |
| 5.5 | 60 | 60 | 30 |
| 6.0 | 60 | overnight | overnight |

Figure 9A:
FIG. 9 shows a tissue dressing comprising a chitosan according to the invention before (9a), during (9b), and after (9c) the application of the detachment solvent.
Figure 9B:
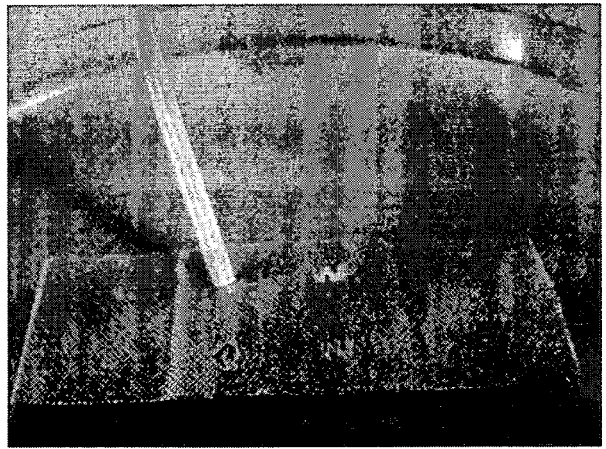
Figure 9C:

In another dissolution experiment, a film C (3×1 cm²) was fixed on the inside of a commercial perforated band-aid (5×2 cm) which was then fixed on a Petri dish. An acetic acid/acetate buffered solution (pH 5.5) was added dropwise through the perforations of the band-aid causing the wound dressing material film to dissolve. The side of the tissue dressing comprising the film is shown in FIG. 9a before and in FIG. 9c after application of the solution. The application of the solution to the band-aid side of the wound dressing is shown in FIG. 9b.

23. Analysis of Non-Soluble and Soluble Fractions of Low-DA Chitosan 0.1 g samples of chitosan with a DA of 1.5%, prepared as described in Example 2, were placed each in 10 ml of phosphate-buffered solution and kept at room temperature under gentle shaking at pH 7.4. At the time points given in Table X, the mixture was filtered, and the non-soluble chitosan remaining in the filter was thoroughly washed and finally dried. The amount of the non-soluble chitosan was determined gravimetrically on a laboratory scale. The results are summarized in Table 6:

TABLE 6

|  | Time of storage in PBS | | | | |
|---|---|---|---|---|---|
|  | 1 hour | 8 hours | 1 day | 3 days | 10 days |
| non-soluble chitosan fraction (%) | 95.5 | 93.5 | 84 | 85 | 84.5 |
| soluble chitosan fraction (%) | 4.5 | 6.5 | 16 | 15 | 15.5 |

24. Cell Viability on Low-DA Chitosan

Chitosan films having DAs of 1.5, 4.0, and 14.5%, respectively, were placed in 24-well cell culture plates, and human HaCaT keratinocytes were seeded at a density of $5 \times 10^4$ cells per cm² and cultured for 2 days. Cell viability was determined using the MTS assay (Promega). After 4 h of MTS incubation with the cells, the light absorbance at 490 nm was measured by an ELISA plate reader and subtracted from that of the controls (without cells) to yield the corrected absorbance. Five samples of each DA were studied. FIG. 14 shows the relative light absorbencies α at 490 nm (PS=100%) for the three samples and a control using polystyrene (PS).

25. Cell Growth on Chitosans of Different DA

Human keratinocytes ($5 \times 10^4$ cells per well) were grown in a 24 well plate for 2 days at 37° C. on chitosan films having DAs of 1.5 and 14.5%, respectively. For the tests cells were isolated from human skin and grown until sub-confluency was reached. After 24 h the medium (Keratinocyte medium with Supplement Mix, Promocell) was changed in order to remove non-adherent cells. FIG. 15 gives representative examples of cells grown on chitosan films after 1 day of incubation.

In FIG. 10, schematically a tissue 1 comprising a wound 2 is shown. For better illustration, FIGS. 5 to 8 are not drawn to scale. The liquid chitosan containing composition according to the invention has been applied to the tissue 2 and the constituent water has been allowed to evaporate, leaving behind a film 3 that dresses the tissue 2 including the wound 3. In general, the film 3 is about 10 to 20 µm thick. Advantageously, the film 3 tightly snuggles to the tissue surface 4, including the wound surface 5.

FIG. 11 schematically shows a chitosan in the form of a solid film 6 that is applied to a tissue 1, comprising a wound 2. The solid film is about 80 µm thick. Cavities 7, 8 between the tissue 1 and the chitosan 6 may be filled with water or exudative fluid.

In FIG. 12, a tissue dressing 9 comprising a chitosan film 6 of FIG. 11 as a first layer and a silicon film 10 as a second layer is applied to a tissue 1, comprising a wound 2. The silicon film 10 is about 50 μm tick. Again, cavities 7, 8 between the tissue 1 and the tissue dressing material 6 may be filled with water or exudative fluid. Finally, FIG. 13 shows a tissue dressing 11 applied to a tissue 1 comprising a wound 2, the tissue dressing 11 differing from that 9 of FIG. 12 in that the silicon film 10 is perforated to allow an exchange of air between the tissue 1 and the surrounding though the wound dressing material 6. The perforations have a diameter if between 50 and 100 μm.

The features described in the above description, claims and figures can be relevant to the invention in any combination. The reference numerals in the claims have merely been introduced to facilitate reading of the claims and are by no means meant to be limiting.

Some embodiments of the invention are the following numbered embodiments:

1. A chitosan for use in
   an antimicrobial treatment of a patient's tissue.
2. The chitosan according to embodiment 1, characterized in that
   the treatment is an antibacterial treatment.
3. The chitosan according to embodiment 1 or 2, characterized in that
   the treatment is for at least one of the following or a combination thereof: preventing the risk of a microbial infection, reducing the microbial load of an existing microbial infection, preventing or reducing the spread of a microbial infection.
4. The chitosan according to embodiment 3, characterized in that
   the infection is at least one of the following or a combination thereof: nosocomial infection, infection with multidrug resistant bacterial strains, methicillin-resistant *Staphylococcus aureus* (MRSA) infection, oxacillin-resistant *Staphylococcus aureus* (ORSA) infection, multidrug-resistant *Clostridium difficile* infection, penicillin-resistant *Streptococcus pneumonia* infection, multidrug-resistent *Pseudomonas aeruginosa* infection, multidrug-resistant *Acinetobacter* baumannii infection.
5. The chitosan according to any one of embodiments 1 to 4, characterized in that
   the treatment is locally confined.
6. The chitosan according to any one of embodiments 1 to 5, characterized in that
   the chitosan is native chitosan.
7. The chitosan according to any one of embodiments 1 to 6, characterized in that
   the chitosan's degree of acetylation is 40% or less.
8. The chitosan according to embodiment 7, characterized in that
   the chitosan is deacetylated.
9. The chitosan according to embodiment 1 or 8, characterized in that
   the chitosan is preparable by a method that involves at least two deacetylation steps.
10. The chitosan according to any one of embodiments 1 to 9, characterized in that
    a fraction of more than 10% of the chitosan being present in a form that is insoluble at a pH of 6.5 or greater.
11. The chitosan according to any one of embodiments 1 or 10, characterized in that
    a fraction of more than 1% of the chitosan is present in a form that is soluble at a pH of 6.5.
12. The chitosan according to any one of embodiments 1 to 11, characterized in that
    a fraction of more than 10% of the chitosan has a molecular weight of 10 kD or more.
13. The chitosan according to any one of embodiments 1 or 12, characterized in that
    a fraction of more than 0.1% of the chitosan has a molecular weight of less than 10 kD.
14. A pharmaceutical composition comprising a chitosan for use in
    an antimicrobial treatment of a patient's tissue.
15. The pharmaceutical composition according to embodiment 14, characterized in that
    the pharmaceutical composition comprises the chitosan according to any one of embodiments 1 to 13.
16. The pharmaceutical composition according to any one of embodiments 14 to 16, characterized in that
    the pharmaceutical composition is free of alcohol.
17. The pharmaceutical composition according to any one of embodiments 14 to 17, characterized in that
    the pharmaceutical composition is a liquid.
18. The pharmaceutical composition according to embodiment 18, characterized in that
    the pharmaceutical composition is an aqueous solution of chitosan.
19. The pharmaceutical composition according to any one of embodiments 14 to 16, characterized in that
    the pharmaceutical composition is solid or gel-like.
20. The pharmaceutical composition according to any one of embodiments 14 to 19, characterized in that
    the treatment is locally confined.
21. A method of treating a microbial infection, the method comprising:
    administering to a patient an effective amount of a chitosan or a pharmaceutical composition comprising chitosan.
22. An aqueous solution comprising chitosan.
23. A chitosan or a pharmaceutical composition comprising a chitosan for use in
    an epithelial cell growth stimulating treatment of a patient's tissue.
24. A method of stimulating the growth of epithelial cells the method comprising:
    administering to a patient or to an epithelial cells containing cell culture an effective amount of a chitosan or a pharmaceutical composition comprising chitosan.
25. A tissue dressing material characterized in that it consists of chitosan.
26. The tissue dressing material of embodiments 25, characterized in that
    the chitosan is native chitosan.
27. The tissue dressing material according to any one of embodiment 25 or 26,
    characterized in that the chitosan's degree of acetylation is 40% or less.
28. The tissue dressing material according to embodiment 27, characterized in that
    the chitosan is deacetylated.
29. The tissue dressing material according to embodiment 25 or 28, characterized in that
    the chitosan is preparable by a method that involves at least two deacetylation steps.
30. The tissue dressing material according to any one of embodiments 25 to 29, characterized in that
    a fraction of more than 10% of the chitosan being present in a form that is insoluble at a pH of 6.5 or greater.

31. The tissue dressing material according to any one of embodiments 25 or 30, characterized in that
a fraction of more than 1% of the chitosan is present in a form that is soluble at a pH of 6.5.
32. The tissue dressing material according to any one of embodiments 25 to 31, characterized in that
a fraction of more than 10% of the chitosan has a molecular weight of 10 kD or more.
33. The tissue dressing material according to any one of embodiments 25 or 32, characterized in that
a fraction of more than 0.1% of the chitosan has a molecular weight of less than 10 kD.
34. A tissue dressing material characterized in that it is a composition comprising chitosan.
35. The tissue dressing material according to embodiment 34, characterized in that
the composition comprises the chitosan according to any one of embodiments 25 to 33.
36. The tissue dressing material according to any one of embodiments 34 to 36, characterized in that
the chitosan containing composition is free of alcohol.
37. The tissue dressing material according to any one of embodiments 34 to 37, characterized in that
the chitosan containing composition is a liquid.
38. The tissue dressing material according to embodiment 38, characterized in that
the chitosan containing composition is an aqueous solution of chitosan.
39. The tissue dressing material according to any one of embodiments 34 to 37, characterized in that
the chitosan containing composition is solid or gel-like.

The invention claimed is:

1. A composition comprising chitosan, wherein
(a) the chitosan has a degree of acetylation of 2% or less,
(b) the chitosan consists of a first fraction and a second fraction,
(c) the first fraction
   (i) consists of polymers having a molecular weight of 10 kD or more,
   (ii) forms a deposit on a surface of a material and is insoluble in the material at a pH of 6.5 to 8.0,
   (iii) comprises more than 10% of the total content of chitosan in the composition, and
(d) the second fraction
   (i) consists of oligomers or low molecular weight polymers having a molecular weight of less than 10 kD,
   (ii) penetrates into and is soluble in the material at a pH of 6.5 to 8.0, and
   (iii) comprises more than 1% of the total content of chitosan in the composition.
2. The composition of claim 1, wherein the material is a hydrophilic material, and wherein optionally the material is an aqueous solution or an aqueous suspension.
3. The composition of claim 1, wherein the second fraction of chitosan has a concentration in an interface region of the material in a range of from about 0.01% w/v to about 1.0% w/v.
4. The composition of claim 1, wherein the composition is an aqueous solution.
5. The composition of claim 1, wherein the chitosan is native chitosan.
6. The composition of claim 1, wherein the first fraction of the chitosan forms a solid or gel-like precipitate on the surface of the material or in the material.
7. The composition of claim 1, wherein the composition is aerosolizable, suspensable, sprayable and/or inhalable.
8. A method of disinfecting a material comprising the following steps:
a) providing a composition of claim 1, having a concentration of a chitosan which is equal to or lower than an effective concentration for disinfecting the material;
b) contacting the composition with the material.
9. The method of claim 8, wherein the infection is a bacterial, fungal or viral infection.
10. The method of claim 8, further comprising:
c) forming a deposit of a first fraction of the chitosan on a surface of the material or forming a deposit of a first fraction of the chitosan in the material, wherein optionally the deposit is a solid or gel-like precipitate and/or wherein optionally step c) further comprises evaporating a solvent contained in the deposit.
11. The method of claim 8, further comprising:
d) transporting a second fraction of the chitosan into the material, or dissolving a second fraction of the chitosan in the material.
12. The method of claim 8, wherein the material is a human or animal tissue, wherein optionally the tissue is a healthy tissue, alveole, wound, burn, abrasion, perforation, cut or laceration, or wherein the material is an aqueous suspension or an aqueous suspension, or wherein the material is an inanimate material, which is optionally selected from the group consisting of a clothing, a wallpaper, a medical gown, a medical facecover, a hydrophilic surface in a medical suite, and medical equipment.
13. The method of claim 8, wherein the composition is administered topically and/or wherein the composition is applied drop-wise or by aerolizing, suspending or spraying.
14. The method of claim 8, wherein the composition has a concentration of the chitosan from about 0.05% w/v to about 5.0% w/v.
15. The method of claim 8, wherein the composition is an aqueous solution, wherein optionally the aqueous solution does not contain an organic solubilizer.
16. The method of claim 8, wherein the chitosan is native chitosan.
17. The method of claim 15, wherein the organic solubilizer is an alcohol.
18. A pharmaceutical composition comprising the composition of claim 1.
19. A method of treating wounds, repairing wounds, tissue remodeling of wounds, disinfecting wounds, promoting hemostasis, reducing bacterial growth, treating microbial infections, or simultaneous promoting hemostasis, disinfecting wounds and repairing the tissue of wounds, in a human or animal, the method comprising:
identifying a human or animal in need thereof, and
administering to the human or animal a composition of claim 1.
20. A method of disinfecting of solutions selected from the group consisting of an infusion solution, a nutrition solution and a neutraceutical solution, or for disinfecting or reducing bacterial growth in drinking water for human or animal use, the method comprising contacting the solution or drinking water with a composition of claim 1.
21. The composition of claim 3, wherein the second fraction of chitosan has a concentration in an interface region of the material in a range of from about 0.1% w/v to about 0.9% w/v.
22. The composition of claim 1, wherein the interface region of the material has a depth of 5 mm or less.
23. The composition of claim 1, wherein the interface region of the material has a depth of 2 mm or less.

24. The composition of claim 1, wherein the aqueous solution does not contain an organic solubilizer.

25. The composition of claim 1, wherein the solution has a pH of 5 to 6.

26. The composition of claim 1, wherein the solution has a pH of about 5.5.

27. The method of claim 5, wherein the infection is an infection with multi resistant *S. aureus, E. coli, P. aeruginosa* and/or *B. tuberculosis*.

28. The method of claim 15, wherein the aqueous solution does not contain an alcohol.

29. The method of claim 8, wherein the solution has a pH of 5 to 6.

30. The method of claim 1, wherein the solution has a pH of about 5.5.

31. The method of claim 8, wherein the composition has a concentration of chitosan from about 0.75% w/v to about 1.0% w/v.

32. A method of reducing bacterial growth on a material comprising the following steps:
   a) providing a composition of claim 1, having a concentration of a chitosan which is equal to or lower than an effective concentration for reducing bacterial growth on the material;
   b) contacting the composition with the material.

33. The method of claim 32, further comprising:
   c) forming a deposit of a first fraction of the chitosan on a surface of the material or forming a deposit of a first fraction of the chitosan in the material, wherein optionally the deposit is a solid or gel-like precipitate and/or wherein optionally step c) further comprises evaporating a solvent contained in the deposit.

34. The method of claim 32, further comprising:
   d) transporting a second fraction of the chitosan into the material, or dissolving a second fraction of the chitosan in the material.

35. The method of claim 32, wherein the material is a human or animal tissue, wherein optionally the tissue is a healthy tissue, alveole, wound, burn, abrasion, perforation, cut or laceration, or wherein the material is an aqueous solution or an aqueous solution suspension, or wherein the material is an inanimate material, which is optionally selected from the group consisting of a clothing, a wallpaper, a medical gown, a medical facecover, a hydrophilic surface in a medical suite, and medical equipment.

36. The method of claim 32, wherein the composition is administered topically and/or wherein the composition is applied drop-wise or by aerolizing, suspending or spraying.

37. The method of claim 32, wherein the composition has a concentration of the chitosan from about 0.05% w/v to about 5.0% w/v.

38. The method of claim 32, wherein the composition has a concentration of chitosan from about 0.75% w/v to about 1.0% w/v.

39. The method of claim 32, wherein the composition is an aqueous solution, wherein optionally the aqueous solution does not contain an organic solubilizer.

40. The method of claim 39, wherein the aqueous solution does not contain an alcohol.

41. The method of claim 32, wherein the chitosan is native chitosan.

42. The method of claim 39, wherein the organic solubilizer is an alcohol.

43. The method of claim 32, wherein the solution has a pH of 5 to 6.

44. The method of claim 32, wherein the solution has a pH of about 5.5.

* * * * *